(12) United States Patent
Ishida

(10) Patent No.: US 12,257,396 B2
(45) Date of Patent: *Mar. 25, 2025

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/479,982

(22) Filed: Oct. 3, 2023

(65) Prior Publication Data

US 2024/0024622 A1    Jan. 25, 2024

Related U.S. Application Data

(63) Continuation of application No. 16/525,238, filed on Jul. 29, 2019, now Pat. No. 11,806,481, which is a (Continued)

(30) Foreign Application Priority Data

Mar. 23, 2017  (JP) ................................. 2017-057566
Oct. 24, 2017  (JP) ................................. 2017-205325

(51) Int. Cl.
*A61M 25/00* (2006.01)
*A61M 25/06* (2006.01)
*A61M 1/36* (2006.01)

(52) U.S. Cl.
CPC .... *A61M 25/0026* (2013.01); *A61M 25/0612* (2013.01); *A61M 25/0693* (2013.01); *A61M 1/3653* (2013.01); *A61M 2025/0681* (2013.01)

(58) Field of Classification Search
CPC .......... A61M 25/0026; A61M 25/0612; A61M 25/0693; A61M 1/3653; A61M 2025/0681
(Continued)

(56) References Cited

U.S. PATENT DOCUMENTS 5,772,636 A      6/1998  Brimhall et al.
2002/0055733 A1* 5/2002  Wilson .................. A61M 25/09
                                                              604/528
(Continued)

FOREIGN PATENT DOCUMENTS

CN      105407952 A      3/2016
JP    2006-297062 A     11/2006
(Continued)

OTHER PUBLICATIONS

Extended European Search Report from EP 18771510.7 dated Apr. 29, 2021.
(Continued)

*Primary Examiner* — Phillip A Gray
(74) *Attorney, Agent, or Firm* — Foley & Lardner LLP

(57) ABSTRACT

A catheter assembly includes: a catheter including a main lumen and one or more sub lumens provided separately from the main lumen; and an inner needle extending through the main lumen; and a deflection suppression mechanism configured to suppress deflection of the inner needle. The one or more sub lumens respectively communicate with one or more sub openings formed in the catheter. The catheter is configured to advance with respect to the inner needle. The deflection suppression mechanism comprises a contact support portion that contacts the catheter when the catheter advances with respect to the inner needle. The contact support portion is configured to contact the catheter at (i) a location proximal of a distal-most one of the one or more sub openings, and/or (ii) a location proximal of a step portion generated in the catheter as the one or more sub lumens are formed.

15 Claims, 18 Drawing Sheets

Related U.S. Application Data continuation of application No. PCT/JP2018/011758, filed on Mar. 23, 2018.

(58) Field of Classification Search
USPC .................................................. 604/164.01
See application file for complete search history.

(56) References Cited

U.S. PATENT DOCUMENTS

| | | |
|---|---|---|
| 2003/0105414 A1 | 6/2003 | Leong |
| 2016/0331939 A1 | 11/2016 | Ishida |
| 2017/0028171 A1 | 2/2017 | Ishida |
| 2017/0172541 A1* | 6/2017 | Yamashita ............... A61B 8/12 |

FOREIGN PATENT DOCUMENTS

| | | |
|---|---|---|
| JP | 2008-043445 A | 2/2008 |
| JP | 2011-167511 A | 9/2011 |
| JP | 2013-034652 A | 2/2013 |
| JP | 2015-000270 A | 1/2015 |
| JP | 2016-503330 A | 2/2016 |
| WO | WO-2006/090637 A1 | 8/2006 |
| WO | WO-2013/137348 A1 | 9/2013 |
| WO | WO-2016/035539 A1 | 3/2016 |

OTHER PUBLICATIONS

Extended European Search Report issued in connection with EP Appl. Ser. No. 22199879.2 dated Jan. 19, 2023.

International Searching Authority and Written Opinion issued in connection with International Patent Application No. PCT/JP2018/011758, dated Jun. 26, 2018.

International Searching Authority, "International Search Report," issued in connection with International Patent Application No. PCT/JP2018/011758, dated Jun. 26, 2018.

International Searching Authority, "Written Opinion," issued in connection with International Patent Application No. PCT/JP2018/011758, dated Jun. 26, 2018.

Office Action dated Jun. 7, 2021 issued in a corresponding Chinese Patent Application No. 201880004084.2.

* cited by examiner

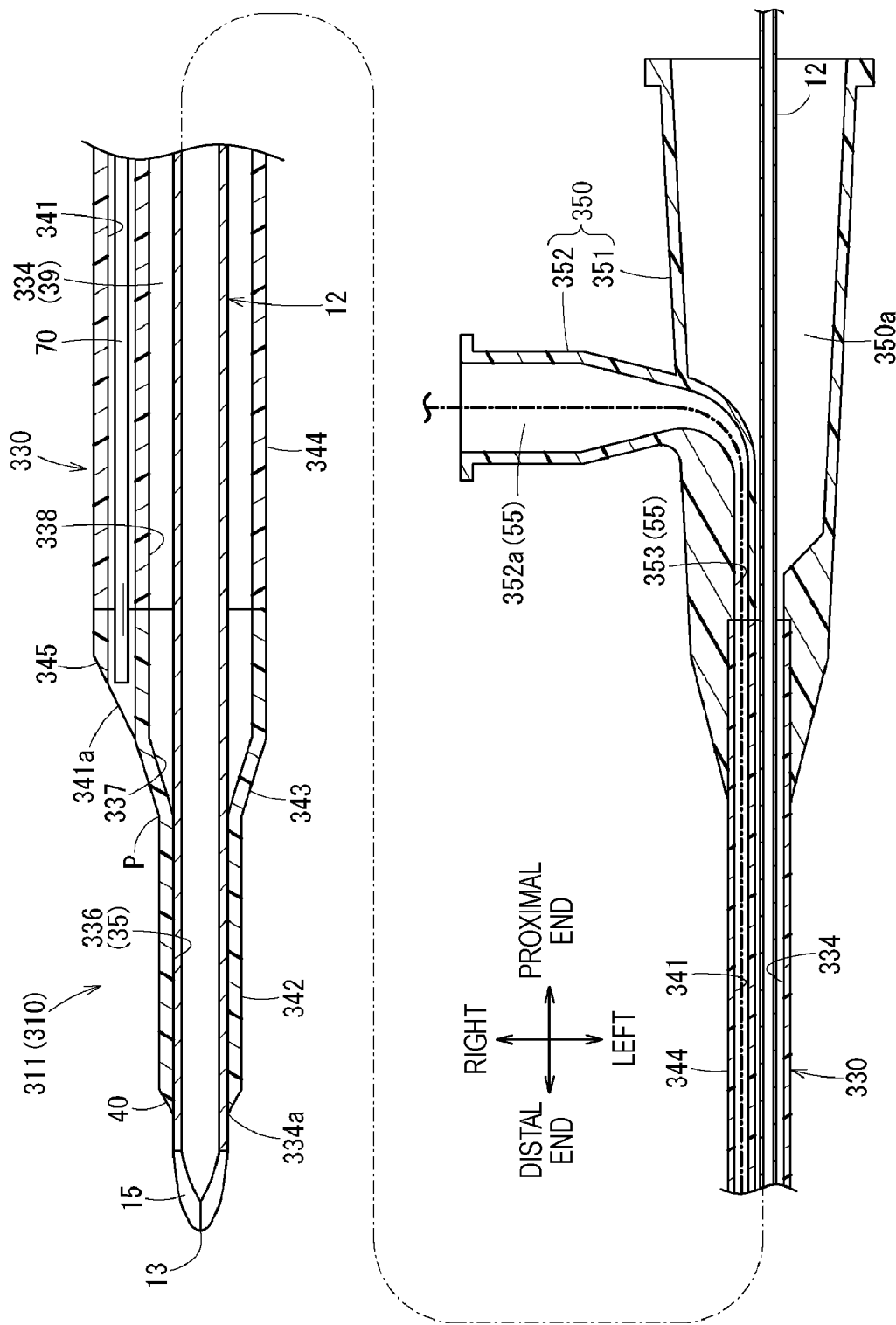

CATHETER ASSEMBLY

CROSS-REFERENCE TO RELATED APPLICATIONS

This is a continuation of U.S. application Ser. No. 16/525,238, filed on Jul. 29, 2019, which is a bypass continuation of PCT Application No. PCT/JP2018/011758, filed on Mar. 23, 2018, which claims priority to Japanese Application Nos. 2017-057566, filed on Mar. 23, 2017, and 2017-205325, filed on Oct. 24, 2017. The contents of these applications are hereby incorporated by reference in their entireties.

BACKGROUND

Technical Field

The present disclosure relates to a catheter assembly used in a case where infusion, blood transfusion, or the like is performed.

Related Art

A catheter assembly having a multi-structure needle in which an inner needle is inserted through a catheter (outer needle) is used as disclosed in, for example, JP 2008-43445 A when an introduction portion for infusion or blood transfusion is constructed for a patient. In using the catheter assembly, a user performs puncturing on the patient with the multi-structure needle, advances the catheter relative to the inner needle, inserts the catheter into a blood vessel, and indwells the catheter by detaching the inner needle from the catheter.

In a case where a plurality of types of drugs may affect each other during administration of the drugs, a plurality of catheters are inserted and indwelled into a patient and the drugs are separately administered. The insertion and indwelling of the plurality of catheters into the patient lead to inconvenience such as the patient's significantly restricted motion and an increase in the patient's burden. In addition, the patient's blood may have to be sampled during the drug administration depending on treatments.

Conceivable in this regard is insertion of a catheter having a plurality of lumens. However, large piercing resistance results from an attempt to insert the catheter having the plurality of lumens in reliance solely on puncturing with an inner needle. This is because the catheter is thicker than the inner needle and this leads to a problem that the catheter cannot be inserted with ease and smoothness.

SUMMARY

Certain embodiments of the present invention have been made in view of the above circumstances, and an object of certain embodiments is to provide a catheter assembly with which a catheter having a plurality of lumens can be inserted with ease and various treatments such as administration of a plurality of types of drugs and blood sampling can be carried out well as a result.

According to one embodiment, a catheter assembly according includes a catheter having a first lumen and a second lumen and an inner needle inserted through the first lumen, in which the inner needle is provided with an introduction path for flashback confirmation allowing blood to flow between the catheter and the inner needle and a gap between an outer peripheral surface of the inner needle and a first inner peripheral surface of the first lumen continuous with a distal end of the catheter is narrower than a gap between the outer peripheral surface of the inner needle and a second inner peripheral surface constituting most of an inner peripheral surface of the first lumen on a proximal end side of the first inner peripheral surface.

In the catheter of the catheter assembly, the first inner peripheral surface of the first lumen is in close contact with or proximity to the outer peripheral surface of the inner needle, while a gap is formed between the outer peripheral surface of the inner needle and the second inner peripheral surface of the first lumen. Accordingly, at the position of the first inner peripheral surface, the catheter is reliably supported by the inner needle even if pressure is received from a biological tissue during puncturing, and thus deflection, shrinkage, and the like of the catheter are suppressed. Accordingly, the distal end of the catheter is smoothly inserted into the body. In addition, the gap of the first lumen smoothens the relative movements of the inner needle and the catheter by suppressing the sliding resistance between the catheter and the inner needle, and thus the operability during catheter insertion and inner needle removal is improved. Further, a user can satisfactorily recognize blood vessel securing because the introduction path allows blood to flow when the inner needle has reached a blood vessel. In other words, the catheter having the plurality of lumens can be easily inserted with the catheter assembly and various treatments such as administration of a plurality of types of drugs and blood sampling can be carried out well with the catheter assembly.

Preferably, the first inner peripheral surface blocks a gap formed between the outer peripheral surface of the inner needle and the second inner peripheral surface by forming a close contact portion coming into close contact with the outer peripheral surface of the inner needle.

The distal end side of the catheter can be reduced in thickness in terms of outer shape and is more reliably supported by the inner needle as the first inner peripheral surface forms the close contact portion with the inner needle. Accordingly, the insertion performance of the catheter is significantly enhanced.

The outer peripheral surface of the catheter may be provided with a second outer peripheral surface positioned in a place of formation of the second inner peripheral surface, a first outer peripheral surface positioned in a place of formation of the first inner peripheral surface and thinner in outer diameter than the second outer peripheral surface, and a tapered outer peripheral surface tapered from the second outer peripheral surface toward the first outer peripheral surface.

In the catheter, the first outer peripheral surface is thinner than the second outer peripheral surface, and thus the catheter can be easily inserted into a blood vessel from the distal end. The tapered outer peripheral surface is inserted subsequently to the first outer peripheral surface, and then the second outer peripheral surface is inserted. Accordingly, the thick second outer peripheral surface can be inserted with ease.

Preferably, the catheter has a main body portion constituting most in an axial direction and a flexible portion provided at a distal end of the main body portion and configured to be more flexible than the main body portion.

In the catheter having the flexible portion, the flexible portion that is in contact with the wall of the blood vessel is easily deflected and curved along the blood vessel during insertion into the blood vessel, and thus inflammation or damage occurrence with respect to the blood vessel wall can be significantly reduced and blood vessel insertability is improved. The first inner peripheral surface of the catheter is supported by the inner needle, and thus the occurrence of deflection or shrinkage of the flexible portion can be effectively suppressed during the insertion that is performed before the blood vessel is reached.

Preferably, an opening on a distal end side of the second lumen is positioned closer to a distal end side than a proximal end of the introduction path in an axial direction of the catheter.

In the catheter assembly, the opening on the distal end side of the second lumen is positioned closer to the distal end side than the proximal end of the introduction path. Accordingly, the blood that flows into the second lumen can be quickly confirmed.

Alternatively, an opening on a distal end side of the second lumen may be positioned closer to a proximal end side than a proximal end of the introduction path in an axial direction of the catheter.

In the catheter assembly, the opening on the distal end side of the second lumen is positioned closer to the proximal end side than the proximal end of the introduction path. Accordingly, the vicinity of the distal end of the catheter can be reduced in thickness and insertability can be improved. In addition, the blood that flows into the first lumen can be quickly confirmed.

An opening on a distal end side of the second lumen can be configured to be provided so as to face a side of the catheter.

Piercing resistance can be reduced by the opening on the distal end side of the second lumen facing the side of the catheter.

Alternatively, an opening on a distal end side of the second lumen may be configured to be provided so as to face a distal direction of the catheter.

By the opening on the distal end side of the second lumen facing the distal direction of the catheter, blocking of the opening by the wall of a blood vessel in a state of being indwelled in the blood vessel is suppressed. Blood can be suctioned well from the opening of the second lumen in particular.

Preferably, a diameter of the second lumen is constant over an entire axial length of the catheter.

In the catheter, the second lumen has a constant diameter, and thus a stable drug flow can be achieved and a guide wire or a stylet can be disposed in a slidable manner.

Preferably, an axially elongated rod-shaped member is detachably disposed in the second lumen.

In the catheter assembly, the rod-shaped member is detachably disposed in the second lumen. Accordingly, the rigidity and the straightness of the catheter can be improved by the rod-shaped member and the catheter can be inserted in a more satisfactory manner.

Here, the catheter assembly can be configured such that the second inner peripheral surface of the first lumen is larger in diameter than an inner peripheral surface of the second lumen.

Alternatively, the catheter assembly can be configured such that the second inner peripheral surface of the first lumen is smaller in diameter than an inner peripheral surface of the second lumen.

The second lumen may be formed in a direction constituting a circumferential direction of the catheter and faced by a blade surface of the inner needle exposed from the first lumen.

In addition, the second lumen may be formed in a direction orthogonal to a direction constituting a circumferential direction of the catheter and faced by a blade surface of the inner needle exposed from the first lumen.

Further, the second lumen may be formed in a direction opposite to a direction constituting a circumferential direction of the catheter and faced by a blade surface of the inner needle exposed from the first lumen.

In other words, the catheter assembly can be appropriately designed with regard to the sizes of the first lumen and the second lumen and the disposition relationship between the lumens in view of factors such as catheter insertability, effects on blood vessels, and flashback visibility.

The catheter assembly may include a first catheter hub fixing and holding the catheter and having a first space communicating with the first lumen and a second catheter hub connected to the first catheter hub and having a second space communicating with the second lumen. A communication path allowing the second lumen and the second space to communicate with each other by bypassing the first space may be provided in the first catheter hub.

The first and second catheter hubs are capable of enhancing connection to a connector of a tube for infusion or blood transfusion. The second space of the second catheter hub and the second lumen of the catheter communicate with each other by means of the communication path in particular, and thus it is possible to cause drugs and blood to flow well.

Preferably, the catheter assembly is provided with a deflection suppression mechanism supporting the catheter and an opening on a distal end side of the second lumen is closer to a distal end side than the deflection suppression mechanism in an assembled state.

In the catheter assembly, the opening on the distal end side of the second lumen is closer to the distal end side than the deflection suppression mechanism. Accordingly, the sliding resistance with respect to the deflection suppression mechanism during a catheter advancement can be reduced as compared with a case where the opening is on the proximal end side. In addition, it is possible to prevent damage to the catheter attributable to the deflection suppression mechanism hitting against the opening of the second lumen during a catheter movement.

Alternatively, the catheter may be provided with a tapered portion increasing in outer diameter toward a proximal direction from a position at a predetermined distance from a distal end of the catheter and the tapered portion may be closer to a distal end side than the deflection suppression mechanism in an assembled state.

In the catheter assembly, the tapered portion is closer to the distal end side than the deflection suppression mechanism. Accordingly, the sliding resistance of the catheter can be reduced as described above, damage to the catheter attributable to the deflection suppression mechanism hitting the tapered portion can be prevented, and inner needle deflection can be prevented by means of step elimination. During catheter advancement, the deflection suppression mechanism holds the large-diameter portion of the catheter without holding the small-diameter portion of the catheter, and thus inner needle deflection can be effectively prevented.

According to another embodiment, a catheter assembly includes an inner needle, a catheter having a main lumen through which the inner needle is detachably inserted and one or more sub lumens provided separately from the main lumen, and a deflection suppression mechanism suppressing deflection of the inner needle by supporting the inner needle via the catheter, in which the one or more sub lumens respectively communicate with one or more sub openings formed in the catheter, the deflection suppression mechanism has a sliding contact support portion rubbing against the catheter when the catheter advances with respect to the inner needle, and the sliding contact support portion is capable of supporting a proximal end side beyond the sub opening on a most distal side among the one or more sub openings or a proximal end side beyond a step portion generated in the catheter as the sub lumen is formed.

The deflection suppression mechanism supports the proximal end side of the sub opening on the most distal side even in the configuration in which the catheter assembly has a plurality of lumens, that is, the main lumen and the one or more sub lumens. As a result, damage to the catheter can be reduced and deflection of the inner needle can be suppressed at the same time. In other words, in the catheter assembly, the position of formation of the sub opening and the support position of the deflection suppression mechanism are appropriately disposed, and thus both deflection prevention for the inner needle and catheter mobility can be achieved. Accordingly, the catheter having the plurality of lumens can be inserted with ease, and thus various treatments such as administration of a plurality of types of drugs and blood sampling can be carried out well.

In this case, the deflection suppression mechanism may be capable of supporting a proximal end side beyond the sub opening on a most proximal end side among the one or more sub openings.

By the proximal end side beyond the sub opening on the most proximal end side being supported, the catheter assembly is capable of more reliably preventing damage to the catheter attributable to the deflection suppression mechanism.

Preferably, the main lumen and the one or more sub lumens extend in parallel to each other in the catheter.

Different types of liquid medicines are allowed to flow well and be administered into a blood vessel by the main lumen and the sub lumens extending in parallel to each other in the catheter assembly.

The step portion may be a tapered portion gradually decreasing in outer diameter toward a distal direction, the one or more sub openings may be provided in the tapered portion, and the deflection suppression mechanism may be capable of supporting a proximal end side beyond the tapered portion.

The catheter assembly is capable of preventing the deflection suppression mechanism from being caught by the tapered portion because the deflection suppression mechanism supports the proximal end side beyond the tapered portion. Accordingly, the mobility of the catheter can be further enhanced.

The one or more sub openings may include a lateral opening provided in an outer peripheral surface of the catheter, and the deflection suppression mechanism may be capable of supporting a proximal end side beyond the lateral opening.

By the sub openings including the lateral opening, the catheter assembly is capable of satisfactorily discharging a liquid medicine and blood into a blood vessel after flowing through the sub lumen. In addition, damage to the lateral opening can be suppressed because the deflection suppression mechanism is positioned closer to the proximal end side than the sub opening.

Preferably, the main lumen communicates with a main opening formed in the catheter and the main opening and the one or more sub openings are apart from each other at a distance of 17 mm or more.

In the catheter assembly, the gap between the main opening and the one or more sub openings is 17 mm or more, and thus a drug flowing out from the sub opening is mixed with a drug flowing out from the main opening after mixing with blood in a blood vessel. In other words, combination contraindications can be administered well with the single catheter.

The deflection suppression mechanism may be capable of supporting a position closer to a distal end side than the deflection suppression mechanism and at a distance of 5 mm or less from the closest one or more sub openings.

In the catheter assembly, the deflection suppression mechanism is capable of supporting the position at a distance of 5 mm or less on the proximal end side of the sub opening. Accordingly, the distance from the needle distal end of the inner needle to the deflection suppression mechanism can be shortened and deflection of the inner needle can be suppressed with more firmness. It is preferable that the deflection suppression mechanism is provided as close as possible to the distal end side from the viewpoint of suppressing the distal end-side deflection of the inner needle and the catheter. As for the catheter having the plurality of lumens, each opening needs to be provided at a certain distance such that a liquid medicine discharged from each opening is mixed in blood. The deflection suppression mechanism being present closer to the distal end side than the opening may lead to damage or the like attributable to contact between the deflection suppression mechanism and the catheter in the vicinity of the opening. Accordingly, both the mixing in blood and deflection suppression can be achieved by the deflection suppression mechanism being provided in the vicinity of the opening and at the limit distance for the mixing of the liquid medicine in blood subsequent to the discharge from each opening as in this feature item.

The main lumen and the one or more sub lumens may be partitioned from each other by a partition wall deformable in response to pressure.

In the catheter assembly, the main lumen and the one or more sub lumens are partitioned from each other by the partition wall, which can be deformed in response to pressure. Accordingly, in a state where the inner needle is inserted before catheter insertion, the relative movements of the catheter and the inner needle can be simplified by the main lumen being enlarged. During drug or blood administration, the partition wall is appropriately deformed by the fluid pressure resulting from the administration. For example, a flow path cross-sectional area can be ensured with ease even in a case where the liquid medicine of the sub lumen is caused to flow by a relatively larger amount than the liquid medicine of the main lumen.

Preferably, the deflection suppression mechanism surrounds an entire circumferential direction of the catheter such that contact is possible.

In the catheter assembly, the deflection suppression mechanism surrounding the entire circumferential direction of the catheter is capable of reliably suppressing upward, downward, leftward, and rightward shaking of the inner needle (such as deviation from the deflection suppression mechanism and deflection of the inner needle).

Here, the catheter assembly may have a catheter hub fixing and holding the catheter and an inner needle hub fixing and holding the inner needle. The one or more sub lumens may communicate with communication paths of one or more ports provided in the catheter hub, and the port may be configured as a connector allowing a medical device to be connected.

It is possible to easily supply a liquid medicine or blood to the one or more sub lumens by a medical device being connected with respect to the port.

In addition to the configurations described above, the inner needle hub may be configured as a housing movably accommodating the catheter hub and the housing may have a slit exposing the port from an inside of the housing to an outside of the housing.

In the catheter assembly, the housing has the slit, and thus the port can be easily moved along the slit even in the configuration in which the catheter hub is provided with the port. In other words, a movement of the catheter with respect to the inner needle can be performed with smoothness.

In this case, the housing may be separable upward and downward, the slit may constitute a part of a boundary of the housing separated upward and downward, and the port may protrude in a lateral direction of the housing.

In the catheter assembly, the port protrudes in the lateral direction of the housing, and thus the port becoming a hindrance during puncturing with the inner needle and the catheter and the like can be suppressed and a user's work can be facilitated.

Alternatively, the port may protrude in an upward direction of the housing.

In the catheter assembly, the port protrudes in the upward direction of the housing. As a result, gripping of the housing can be simplified and operability can be enhanced for users.

The port may have a connecting portion allowing the medical device to be connected and a soft tube extending between the catheter hub and the connecting portion and softer than the connecting portion.

The catheter assembly is provided with the port including the connecting portion and the soft tube, and thus the connecting portion can be freely placed in terms of position and posture. Accordingly, a user can carry out puncturing and catheter insertion.

The port may have a connecting portion allowing the medical device to be connected, a hard tube connected to the catheter hub and protruding to an outside of the inner needle hub, and a soft tube extending between the hard tube and the connecting portion and softer than the connecting portion.

In the catheter assembly, the connecting portion, the hard tube, and the soft tube constitute the port, and thus the hard tube can be placed at the position coming into contact with the inner needle hub and the catheter hub can be smoothly moved.

According to certain embodiments of the present invention, the catheter having the plurality of lumens can be easily inserted with the catheter assembly. As a result, various treatments such as administration of a plurality of types of drugs and blood sampling can be carried out well with the catheter assembly.

BRIEF DESCRIPTION OF DRAWINGS

FIG. 5 is a plan cross-sectional view illustrating a catheter, a catheter hub, and an inner needle of a catheter assembly according to a fourth embodiment;

DETAILED DESCRIPTION

Hereinafter, embodiments of a catheter assembly according to the present invention will be described in detail with reference to accompanying drawings.

First Embodiment

A catheter assembly 10 according to a first embodiment is a medical device that is used in a case where infusion, blood transfusion, or the like is performed on a patient (living body) and constructs an inlet and an outlet for a liquid (liquid medicine or blood) by means of puncturing with a catheter 30 and insertion and placement of the catheter 30 into the patient's body. The catheter assembly 10 is configured to insert a catheter (such as a central venous catheter, a PICC, and a midline catheter) that is longer than a peripheral venous catheter. It should be noted that the catheter assembly 10 may insert a peripheral venous catheter that is shorter than a central venous catheter. In addition, the catheter assembly 10 may insert an arterial catheter such as a peripheral arterial catheter without being limited to venous catheters.

Figure 1:
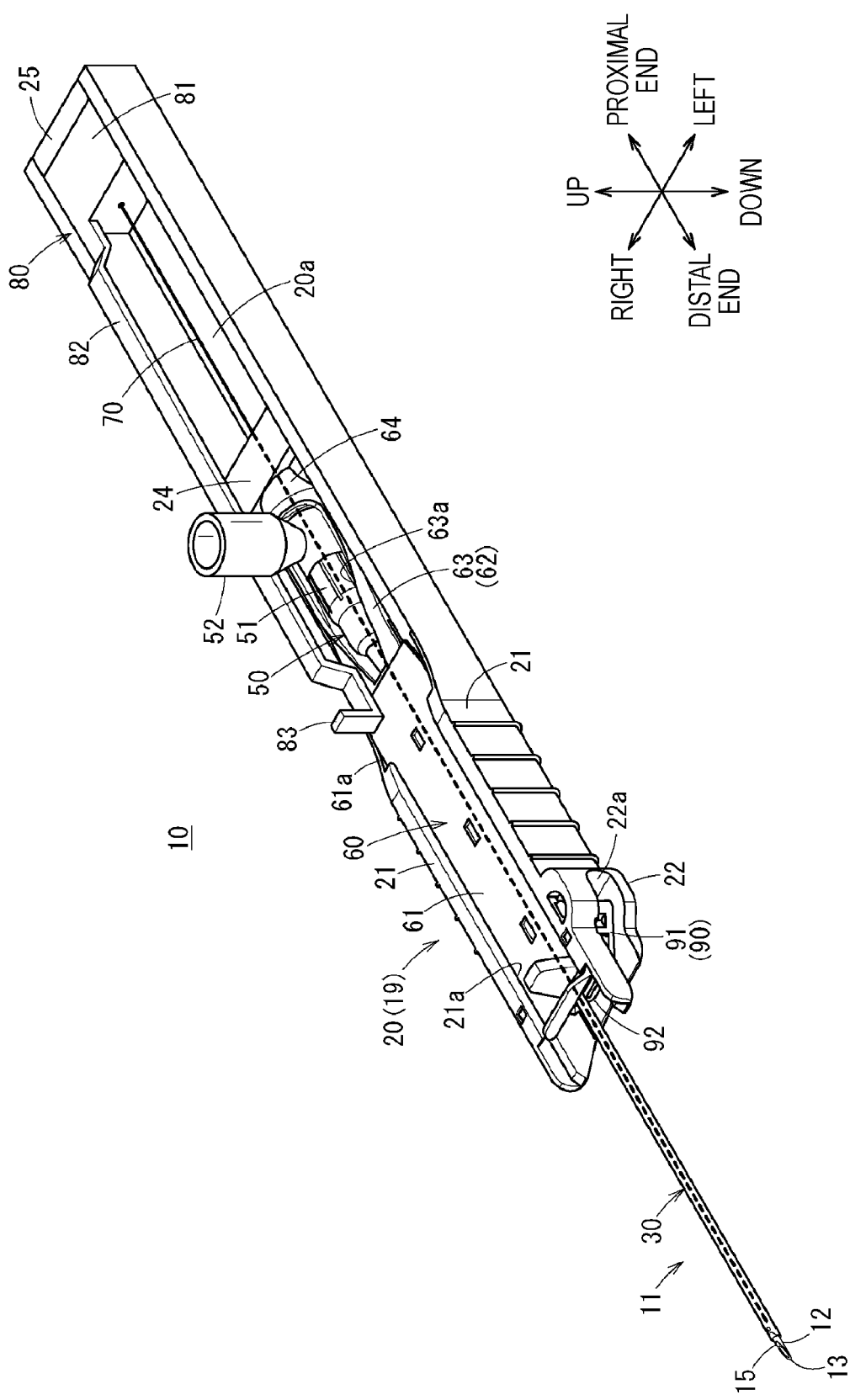
FIG. 1 is a perspective view illustrating an overall configuration of a catheter assembly according to a first embodiment of the present invention.

As illustrated in FIG. 1, the catheter assembly 10 is provided with an inner needle 12, a housing 20 (inner needle hub) fixing and holding the inner needle 12, the catheter 30 disposed outside the inner needle 12, and a catheter hub 50 fixing and holding the catheter 30. Further, the catheter assembly 10 is provided with a catheter operation member 60 operating the catheter 30 and the catheter hub 50 for advancing and retracting movements and a guide wire 70 and a guide wire operation member 80 guiding the advancement of the catheter 30.

Figure 2:
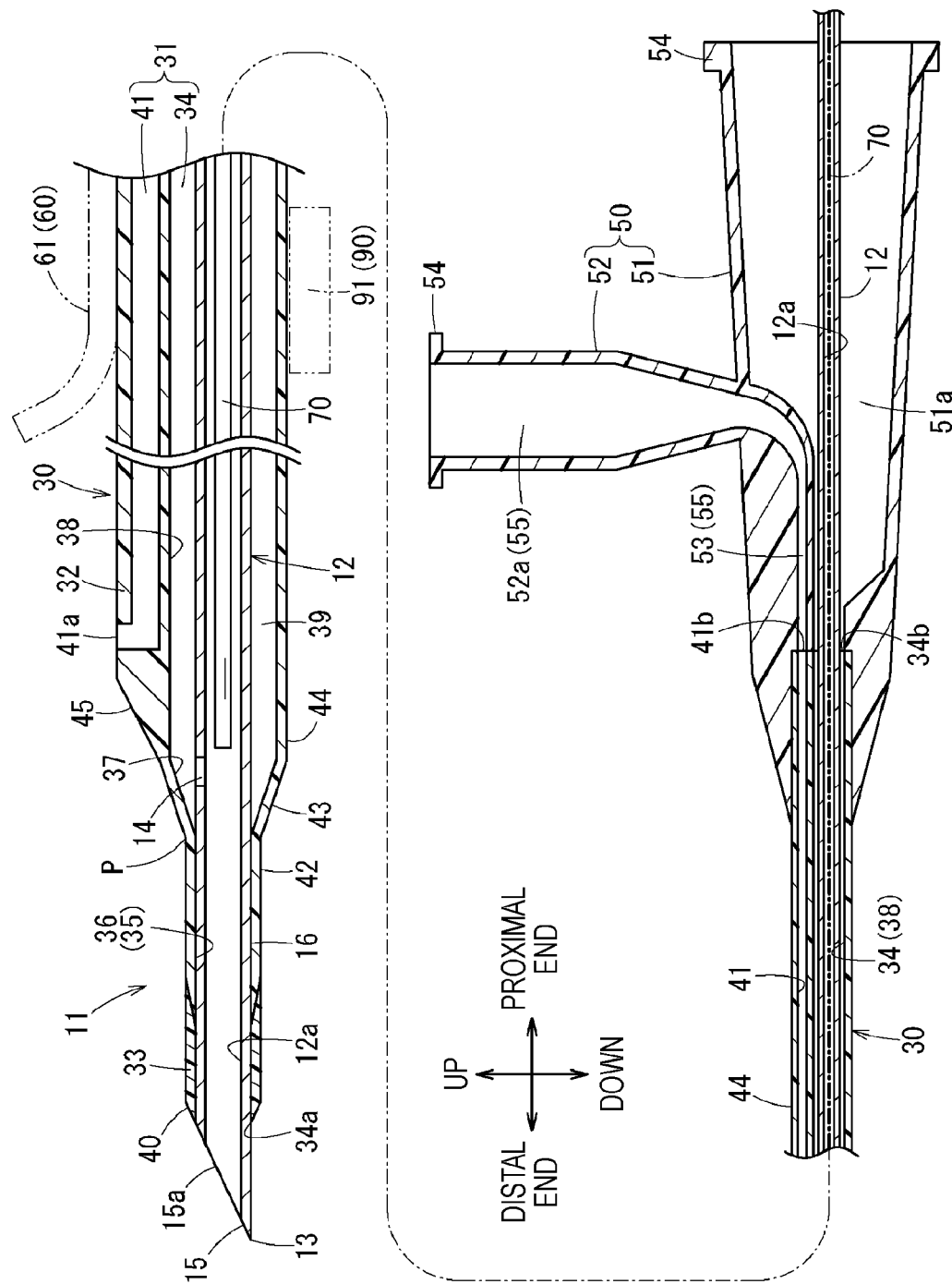
FIG. 2 is a side cross-sectional view illustrating a catheter, a catheter hub, and an inner needle in FIG. 1.

In addition, the catheter 30 according to the present embodiment is configured as a multi-lumen catheter incorporating a plurality of (two in the present embodiment) lumens 31 (see also FIG. 2). In a pre-use assembled state (pre-puncture state), the catheter assembly 10 forms a multi-structure needle 11 with the inner needle 12 inserted through and disposed in a main lumen 34 of one of the plurality of lumens 31 and the guide wire 70 accommodated in the inner needle 12.

As for the multi-structure needle 11, a needle tip 13 of the inner needle 12 protrudes beyond the distal end of the catheter and the guide wire 70 is disposed in the inner needle 12 in the pre-puncture state. The proximal end side of the multi-structure needle 11 is accommodated in the housing 20. The catheter hub 50, the catheter operation member 60, and the guide wire operation member 80 are accommodated in the housing 20 together.

In using the catheter assembly 10, a user such as a doctor and a nurse grips the housing 20 and punctures a patient's body with the multi-structure needle 11. Further, the guide wire 70 is sent out from the inner needle 12 into a blood vessel with the punctured state maintained and the catheter 30 is inserted into the blood vessel along the guide wire 70. Then, the catheter 30 is indwelled into the blood vessel by the inner needle 12 being retracted and removed with respect to the catheter 30. In the indwelling state, the catheter 30 allows the two lumens 31 to communicate with each other in the blood vessel. As a result, the catheter 30 allows treatments such as separate administration of a plurality of types of drugs and blood sampling during drug administration. Hereinafter, each configuration of the catheter assembly 10 will be described in detail.

As illustrated in FIGS. 1 and 2, the inner needle 12 is configured as a rigid hollow tube capable of puncturing the skin of a living body and the sharp needle tip 13 is provided at the distal end of the inner needle 12. A hollow portion 12a is provided along the axial direction of the inner needle 12 in the inner needle 12. It should be noted that the inner needle 12 may be a solid structure that is not provided with the hollow portion 12a.

The needle tip 13 has a blade surface 15 that is inclined at a predetermined angle with respect to the axial center of the inner needle 12 by a cylindrical tube being obliquely cut. The blade surface 15 has an elliptical shape surrounding a distal end opening 15a communicating with the hollow portion 12a. When the catheter assembly 10 is used, the blade surface 15 is directed in the direction that faces the user (upward direction in a case where the surface of a patient's body is a lower side). As a result, the edge of the blade surface 15 cuts the skin and is inserted into the body during puncturing.

Hereinafter, the direction and the position of each configuration of the catheter assembly 10 will be described based on the direction of the blade surface 15 unless otherwise specified (see also the arrow directions in FIG. 1).

Especially, the disposition of the plurality of lumens 31 of the catheter 30 will be described in relation to the blade surface 15.

It should be noted that the shape of the blade surface 15 is not particularly limited although FIGS. 1 and 2 exemplify the blade surface 15 that is simply cut obliquely with respect to the axial center of the inner needle 12. For example, the needle tip 13 may have a lancet-type configuration in which two inclined left and right blade surfaces 15 form a distal end (peak) at the center in the width direction or a back-cut configuration in which the opposite side of the blade surface 15 is cut.

The inner needle 12 is provided with a hole portion 14 penetrating the outer surface and the hollow portion 12a. In other words, the inner needle 12 constitutes an introduction path for blood flashback confirmation during puncturing with the multi-structure needle 11 by means of the distal end opening 15a, the hollow portion 12a, and the hole portion 14.

Examples of the constituent material of the inner needle 12 include a hard resin, ceramics, and a metal material such as stainless steel, aluminum or an aluminum alloy, and titanium or a titanium alloy. The inner needle 12 is firmly fixed to the housing by appropriate fixing means such as fusion, adhesion, and insert molding.

The housing 20 of the catheter assembly 10 is an inner needle hub 19 fixing and holding the inner needle 12 and moving integrally with the inner needle 12 and constitutes a grip part that a user grips. The housing 20 has an elongated bowl shape as a whole. The housing 20 is designed so as to have a moderate size (thickness and length) such that a user grips the housing 20 with ease.

The housing 20 is provided with an accommodating space 20a accommodating the catheter hub 50, the catheter operation member and the guide wire operation member 80. A pair of side walls 21 sandwiching the accommodating space 20a extend in parallel in the longitudinal direction. The side walls 21 have groove-shaped rail portions 21a in the inner surfaces that are on the distal end side, which is formed higher than the proximal end side. The pair of rail portions 21a slidably accommodate a side edge 61a of the catheter operation member 60. The distal end side of one of the pair of side walls 21 (side wall 21 in the leftward direction in FIG. 1) has a bulging portion 22, which bulges outward in the width direction. A support member 91, which is a deflection suppression mechanism 90, is attached to a disposition recess 22a of the bulging portion 22.

The support member 91 has a sliding contact support portion 92 that allows the accommodating space 20a of the housing 20 to protrude in the rightward direction and is rotatably and pivotally supported by the side wall 21. The sliding contact support portion 92 rubs against the catheter 30 when the catheter 30 (multi-structure needle 11) held by the catheter operation member advances. The sliding contact support portion 92 may not be in contact with the catheter 30 before the catheter 30 is used or during a movement of the catheter 30 relative to the housing 20. In addition, the support member 91 has, in the upper end portion of the support member 91, a groove portion (not illustrated) accommodating the side edge 61a of the catheter operation member in a state where the catheter operation member 60 is accommodated in the housing 20. The presence of the side edge 61a in the groove portion results in regulation of rotation and standing by for the catheter 30 to be supportable. When the catheter operation member advances, the support member 91 becomes rotatable by the side edge 61a coming out of the groove portion. Further, the support member 91 rotates toward the outside of the side wall 21 by contact of the catheter operation member 60. As a result, the catheter hub and the catheter operation member 60 are smoothly sent out from the housing 20 with the support member 91 (sliding contact support portion 92) remaining in the housing 20.

The housing 20 is provided with a block-shaped needle holding portion 24, which holds the inner needle 12 at the axially intermediate position of the accommodating space 20a. A guide mechanism (not illustrated) is provided on the side of the housing that is closer to the proximal end than the needle holding portion 24. The guide mechanism guides sliding of the guide wire operation member 80 and regulates detachment of the guide wire operation member 80. Further, a rear wall 25 closing the accommodating space 20a is provided on the most proximal end side of the housing 20.

The constituent material of the housing 20 is not particularly limited. For example, a thermoplastic resin such as polypropylene, polycarbonate, polyamide, polysulfone, polyarylate, and a methacrylate-butylene-styrene copolymer may be applied. It should be noted that the housing 20 may be formed in a square tube shape in which, for example, the accommodating space 20a is covered with an upper wall although the housing 20 has a configuration in which the upper surface of the accommodating space 20a is exposed in the illustrated example.

The catheter 30 of the catheter assembly 10 is formed in the shape of a perfect circle in a cross-sectional view orthogonal to the axial direction and extends with an appropriate length along the axial direction. The length of the catheter 30 is not particularly limited and can be appropriately designed in accordance with applications, conditions, and so on. For example, the catheter 30 has a set length of approximately 14 to 500 mm.

As illustrated in FIG. 2, a main body portion 32 and a soft tip 33 (flexible portion) constitute the catheter 30. The main body portion 32 constitutes most of the catheter 30 in the axial direction. The soft tip 33 is provided at the distal end of the main body portion 32 and is softer than the main body portion 32. The main body portion 32 and the soft tip 33 are firmly fixed by an appropriate fixing method such as heat fusion and adhesion, and the outer peripheral surfaces of the main body portion 32 and the soft tip 33 are continuously formed in series. The main body portion 32 and the soft tip 33 have connection boundary portions overlapping each other in a tapered shape. As a result, the physical properties of the catheter 30 are gradually changed.

The plurality of lumens 31 in the catheter 30 include the main lumen 34 (first lumen) in which the inner needle 12 is inserted through and disposed in the pre-puncture state and a sub lumen 41 (second lumen) extending in parallel with the main lumen 34. Each of the main lumen 34 and the sub lumen 41 is formed in the shape of a perfect circle in a cross-sectional view orthogonal to the axis of the catheter 30.

The main lumen 34 is provided over the entire axial length of the catheter 30 and communicates with a first distal end opening 34a (main opening) formed at the distal end of the catheter 30 and a first proximal end opening 34b formed at the proximal end of the catheter 30. The first distal end opening 34a exposes the needle tip 13 of the inner needle 12.

The inner peripheral surface of the catheter 30 that constitutes the main lumen 34 is divided into a first inner peripheral surface 36 and a second inner peripheral surface 38 based on a predetermined axial position P. In this embodiment, there is no gap between the first inner peripheral surface 36 and an outer peripheral surface 16 of the inner needle 12. A gap 39 is formed between the second inner peripheral surface 38 and the outer peripheral surface 16 of the inner needle 12. A tapered inner peripheral surface 37 interconnecting the first inner peripheral surface 36 and the second inner peripheral surface 38 is formed at the distal end of the second inner peripheral surface 38.

The diameter of the first inner peripheral surface 36 is equal to or slightly smaller than the outer diameter of the outer peripheral surface 16 of the inner needle 12. As a result, the first inner peripheral surface 36 forms a close contact portion 35 coming into close contact with the outer peripheral surface 16 of the inner needle 12 and closes the gap 39 of the second inner peripheral surface 38. Accordingly, the diameter of the first inner peripheral surface 36 may be designed in accordance with the outer diameter of the inner needle 12 and may range, for example, from 0.3 mm to 1.8 mm. The longitudinal (axial) length of the first inner peripheral surface 36 may range, for example, from 0.1 mm to 4.0 mm so that the distal end of the catheter 30 is inserted well.

The soft tip 33 and the main body portion 32 constitute the distal end of the catheter 30. The inside of the distal end of the catheter 30 forms the first inner peripheral surface 36 (close contact portion 35). The most distal end of the first inner peripheral surface 36 of the soft tip 33 forms the first distal end opening 34a. The most distal end that is on the outer peripheral surface side of the soft tip 33 is formed in, for example, a distal end tapered portion 40, which has the same inclination as the blade surface 15 of the needle tip 13 (or is less inclined than the blade surface 15).

The tapered inner peripheral surface 37 of the main lumen 34 has a diameter that gradually decreases toward the distal direction (first inner peripheral surface 36) in a short axial range. A second inner peripheral surface 38 constitutes the inner peripheral surface of most of the main lumen 34 in the axial direction.

The diameter of the second inner peripheral surface 38 is formed so as to be larger than the outer diameter of the outer peripheral surface 16 of the inner needle 12. As a result, the inner needle 12 and the catheter 30 can be slid well. In the pre-puncture state, the hole portion 14 of the inner needle 12 faces the second inner peripheral surface 38 and communicates with the gap 39 of the second inner peripheral surface 38. Accordingly, blood flashback can be performed well in the gap between the inner needle 12 and the catheter 30. The designed diameter of the second inner peripheral surface 38 may be, for example, approximately 1.02 to 1.33 times the diameter of the first inner peripheral surface 36.

The sub lumen 41 is provided separately from the main lumen 34 along the axial direction of the catheter 30. In other words, the main lumen 34 and the sub lumen 41 extend in the catheter 30 along mutually parallel axes. The sub lumen 41 is bent radially outward at a midway position on the distal end side of the catheter 30 and communicates with a second lateral opening 41a (sub opening) formed in the outer peripheral surface (side) of the catheter 30.

The second lateral opening 41a is positioned closer to the proximal end side than the first distal end opening 34a. Preferably, the distance between the first distal end opening 34a and the second lateral opening 41a is 17 mm or more.

In the catheter assembly 10, the distance between the first distal end opening 34a and the second lateral opening 41a is 17 mm or more, and thus a drug flowing out from one of the first distal end opening 34a and the second lateral opening 41a is mixed with a drug flowing out from the other after mixing with blood in a blood vessel. In other words, combination contraindications can be administered well with the single catheter 30. It should be noted that the proximal end side of the sub lumen 41 communicates with a second proximal end opening 41b and the second proximal end opening 41b is adjacent to the first proximal end opening 34b.

In the present embodiment, the diameter of the inner peripheral surface of the sub lumen 41 is set to a dimension that is smaller than the diameter of the inner peripheral surface of the main lumen 34 (first inner peripheral surface 36). In other words, the plurality of lumens 31 are constituted by the large-diameter main lumen 34 where the inner needle 12 is disposed and the small-diameter sub lumen 41 where nothing is disposed. Further, the inscribed circle diameter of the sub lumen 41 is constant along the axial direction of the catheter 30 whereas the diameter of the main lumen 34 changes along the axial direction. The diameter of the sub lumen 41 is not particularly limited insofar as a drug is allowed to flow in from the second proximal end opening 41b and the drug can be guided to the second lateral opening 41a. For example, the sub lumen 41 has a diameter ranging from 0.3 to 1.2 mm.

The outer peripheral surface of the catheter 30 has a distal end-to-predetermined position P range formed in the first outer peripheral surface 42 with a small-outer diameter. For example, the first outer peripheral surface 42 is one size larger in outer diameter than the inner needle 12. In addition, the outer peripheral surface of the catheter 30 has a tapered outer peripheral surface 43 increasing in thickness from the predetermined position P toward the proximal direction and the second outer peripheral surface 44 continuous with the proximal end of the tapered outer peripheral surface 43 and thicker than the first outer peripheral surface 42. The second outer peripheral surface 44 is provided at the position where the sub lumen 41 is formed.

In the catheter 30, the first inner peripheral surface 36 and the first outer peripheral surface 42 overlap each other, the tapered inner peripheral surface 37 and the tapered outer peripheral surface 43 overlap each other, and the second inner peripheral surface 38 and the second outer peripheral surface 44 overlap each other in the axial direction of the catheter 30. Accordingly, in this configuration, the thickness of the main body portion 32 itself does not change in the vicinity of the predetermined position P. In other words, in the vicinity of the predetermined position P, continuity is provided with the thickness of the main body portion 32 constant even if the shape of the main body portion 32 becomes thin. In addition, a continuous inclined surface 45, which is inclined continuously with the tapered outer peripheral surface 43 and is continuous with the second outer peripheral surface 44, is provided at the position where the outer diameter increases to the same extent as the formation of the sub lumen 41.

The constituent material of the main body portion 32 is not particularly limited. A soft resin material is preferable as the constituent material of the main body portion 32. Examples of the constituent material of the main body portion 32 include fluororesins such as polytetrafluoroethylene (PTFE), ethylene-tetrafluoroethylene copolymer (ETFE), and perfluoroalkoxy fluorine resin (PFA), olefin-based resins such as polyethylene and polypropylene or mixtures of the resins, polyurethane, polyester, polyamide, a polyether nylon resin, and a mixture of an olefin-based resin and an ethylene-vinyl acetate copolymer. The constituent material of the soft distal end 33 is not particularly limited. For example, a resin material such as polyurethane may be applied as the constituent material of the soft tip 33.

Preferably, the catheter 30 is formed of a material having transparency. Then, a user can visually and satisfactorily recognize the flashback of the blood that has flowed into the main lumen 34 and the sub lumen 41. It should be noted that the catheter 30 may have a configuration in which the flesh portion that constitutes the main lumen 34 has transparency and the flesh portion that constitutes the sub lumen 41 has opacity. This is because a user can visually recognize the blood by the blood flowing around into the gap 39. In an alternative configuration, the flesh portion that constitutes the sub lumen 41 may have transparency and the flesh portion that constitutes the main lumen 34 may have opacity. The flashback can be confirmed with the catheter assembly 10 even in a configuration in which the inner needle 12 does not have the hole portion 14 (notch). This is because blood flows into the main lumen 34 at a stage in which contact between the distal end side of the inner needle 12 and the inner peripheral surface of the main lumen 34 of the catheter 30 has disappeared as the catheter 30 advances relative to the inner needle 12.

The proximal end portion of the catheter 30 is fixed to the distal end portion in the catheter hub 50 by appropriate fixing means such as caulking, fusion, and adhesion. The catheter hub 50 is exposed on a patient's skin in a state where the catheter 30 is inserted in the patient's blood vessel, is affixed with a tape or the like, and is indwelled together with the catheter 30. The material that constitutes the catheter hub 50 is not particularly limited. For example, the materials listed for the housing 20 may be appropriately adopted.

As illustrated in FIGS. 1 and 2, the catheter hub 50 has a main hub 51 (first catheter hub) and a sub hub 52 (second catheter hub). The main hub 51 is formed in the shape of a tube tapered in the distal direction. The sub hub 52 is connected to the side surface of the main hub 51. The main hub 51 constitutes a main port allowing one of two types of drugs to flow in during infusion or the like. The sub hub 52 constitutes a sub port allowing the other of the drugs to flow in.

The main hub 51 fixes and holds the catheter 30 in the distal end portion of the main hub 51 and is provided with a main space 51a (first space) on the proximal end side of the fixing part. The main space 51a communicates with the main lumen 34. In the pre-puncture state, the inner needle 12 is inserted through the main space 51a. A flow path 53 is provided in the main hub 51, communicates with the sub lumen 41 of the catheter 30, and communicates with a sub space 52a in the sub hub 52. The sub space 52a and the flow path 53 constitute a communication path 55 communicating with the sub lumen 41.

The sub hub 52 is formed in a tubular shape having the sub space 52a therein. The sub hub 52 is provided above the main space 51a correspondingly to the disposition relationship between the sub lumen 41 and the main lumen 34 of the catheter 30. As a result, the main hub 51 can be easily manufactured in a shape in which the flow path 53 and the main space 51a are separate from each other. In addition, the housing 20 can be configured to be thin in the width direction and a user can easily grip the housing 20 during puncturing.

The main hub 51 and the sub hub 52 are connecting portions to which an infusion tube connector can be connected (for example, a flange portion 54 protruding radially outward is provided at the proximal end or the inner peripheral surface of the sub space 52a or the main space 51a is formed into a luer taper). It should be noted that the main space 51a of the main hub 51 and the sub space 52a of the sub hub 52 may accommodate, for example, a hemostatic valve (not illustrated) that prevents blood from flowing back and a plug (not illustrated) that allows infusion by penetrating a hemostatic valve as an infusion tube connector is inserted.

The catheter operation member 60 operates the catheter 30 and the catheter hub 50 for a movement relative to the inner needle 12 and the housing 20 as illustrated in FIG. 1. The catheter operation member 60 directly holds the catheter 30 and accommodates and holds the catheter hub 50. The catheter operation member 60 has an operation plate portion 61 extending in the longitudinal direction of the housing 20 and a hub storage portion 62 continuous with the proximal end of the operation plate portion 61 and storing the catheter hub 50.

The operation plate portion 61 is a part that a user advances and retracts with his or her finger. In the pre-puncture state, a pair of the side edges 61a of the operation plate portion 61 are disposed in the pair of rail portions 21a of the housing 20 and the upper surfaces of the pair of side walls 21. At least one catheter holding portion including a pair of projecting pieces (not illustrated) is provided along the longitudinal direction on the lower surface of the operation plate portion 61 and bites the catheter 30 in each place.

In other words, as illustrated in FIGS. 1 and 2, the midway position of the multi-structure needle 11 (catheter 30) in the axial direction is supported by the deflection suppression mechanism 90 that the support member 91 and the operation plate portion 61 constitute. The place of the support by the support member 91 (deflection suppression mechanism 90) is positioned closer to the proximal end side than the tapered outer peripheral surface 43 or the continuous inclined surface 45 and closer to the proximal end side than the second lateral opening 41a. The support member 91 is capable of supporting the catheter 30 in the vicinity of the closest second lateral opening 41a and on the distal end side that is beyond the support member 91.

More specifically, the support member 91 is capable of supporting the catheter 30 on the distal end side that is beyond the support member 91 and at the position that is at a distance of 5 mm or less from the closest second lateral opening 41a. Here, it is preferable that the deflection suppression mechanism 90 is provided as close as possible to the distal end side from the viewpoint of suppressing the distal end-side deflection of the inner needle 12 and the catheter 30. As for the catheter 30 having the main lumen 34 and the sub lumen 41, each opening needs to be provided at a certain distance such that a liquid medicine discharged from each opening is mixed in blood. The deflection suppression mechanism 90 being present closer to the distal end side than the second lateral opening 41a may lead to damage or the like attributable to contact between the deflection suppression mechanism 90 and the catheter 30 in the vicinity of the second lateral opening 41a. Accordingly, both the mixing in blood and deflection suppression can be achieved by the deflection suppression mechanism 90 being provided in the vicinity of the second lateral opening 41a and at the limit distance for the mixing of the liquid medicine in blood subsequent to the discharge from each opening.

The hub storage portion 62 constitutes a storage chamber storing the catheter hub 50 by means of an upper plate 63 continuous with the operation plate portion 61 and a pair of side plates (not illustrated). The upper plate 63 is provided with a disposition hole 63a, which is notched in a substantially isosceles triangle shape in accordance with the shape of the catheter hub 50 and causes the sub hub 52 to protrude. The hub storage portion 62 holds the flange portion 54 of the catheter hub 50 so as to be separable by an appropriate frictional force by means of the pair of side plates and an arch portion 64 providing circular arc-shaped bridging on the proximal end side.

As illustrated in FIGS. 1 and 2, the guide wire 70 of the catheter assembly 10 is disposed in the hollow portion 12a of the inner needle 12 and extends along the axial direction of the inner needle 12. The guide wire 70 extends from the proximal end opening (not illustrated) of the inner needle 12 and is fixed to the guide wire operation member 80. The guide wire 70 is formed so as to be axially longer than the inner needle 12 and has appropriate rigidity and flexibility.

In the pre-puncture state, the distal end of the guide wire 70 is disposed closer to the proximal end side than the hole portion 14 of the inner needle 12. As a result, the blood that has flowed into the hollow portion 12a from a blood vessel during puncturing with the inner needle 12 flows out well to the outside of the inner needle 12 via the hole portion 14 and a user can visually recognize the flashback. In a state of being punctured with the inner needle 12, the guide wire 70 advances into the blood vessel by being sent out from the distal end opening 15a of the inner needle 12 under the operation of the guide wire operation member 80 by the user.

Returning to FIG. 1, the guide wire operation member 80 of the catheter assembly 10 has a holding block 81 fixing and holding the guide wire 70 on the proximal end side of the housing 20 and an operation arm 82 extending in the distal direction from the holding block 81. The distal end portion of the operation arm 82 is provided with an operation projection 83 operated by direct contact with a user and is placed so as to be capable of sliding with respect to the flat upper surface of the guide wire operation member 80. In other words, the holding block 81 advances in conjunction with advancement of the operation arm 82 and the guide wire 70 is pushed out in the distal direction as a result. The guide wire 70 is sent out from the distal end opening 15a of the inner needle 12 in accordance with the amount of advancement of the guide wire operation member 80.

The catheter assembly 10 according to the first embodiment is basically configured as described above. The actions and effects of the catheter assembly 10 will be described below.

The catheter assembly 10 is used in constructing an introduction portion for infusion to a patient as described above. In using the catheter assembly 10, a user grips the housing 20 and performs puncturing on the patient with the multi-structure needle 11. At this time, the support member 91 of the housing 20 supports the second outer peripheral surface 44 of the catheter 30 (place where the plurality of lumens 31 extend) and satisfactorily ensures the linearity of the catheter 30. During puncturing, the catheter 30 is inserted into the body after the inner needle 12 is inserted by the skin and a blood vessel being cut with the blade surface 15.

As illustrated in FIG. 2, during the insertion, the sufficiently thin first outer peripheral surface 42 is inserted first, and thus the catheter 30 undergoes a sufficiently low piercing resistance. In addition, the first inner peripheral surface 36 including the soft tip 33 is in close contact with the inner needle 12, and thus the first inner peripheral surface 36 is not deflected radially inward. As a result, axial shrinkage of the distal end of the catheter 30 is suppressed as well and the catheter 30 is inserted with ease. Especially, a thick needle can be adopted as the inner needle 12 disposed in the main lumen 34, and thus deflection of the catheter 30 is reduced.

When a blood vessel is punctured, the distal end of the guide wire 70 is positioned on the proximal end side of the hole portion 14. Accordingly, the blood that has flowed into the hollow portion 12a of the inner needle 12 flows through the hole portion 14 to the main lumen 34 of the catheter 30 (gap 39 of the second inner peripheral surface 38). As a result, a user can visually recognize the flashback of the blood and confirm that the main lumen 34 has secured the blood vessel.

Once the catheter 30 is further inserted, the catheter 30 moves from the predetermined position P to the tapered outer peripheral surface 43. Although the biological tissue spreads at this time, the catheter 30 can be smoothly inserted along the tapered outer peripheral surface 43. In addition, the smooth insertion of the catheter 30 can be continuously performed by the inclination of the continuous inclined surface 45 even after the continuous inclined surface 45 is reached. Especially, the sub lumen 41 has a small diameter and the rate of change in the outer diameter of the second outer peripheral surface 44 with respect to the first outer peripheral surface 42 is small as well, and thus the piercing resistance of the catheter 30 is significantly suppressed. Accordingly, the catheter 30 can be smoothly inserted up to the second outer peripheral surface 44.

After the multi-structure needle 11 is somewhat inserted into the blood vessel, the user advances the guide wire operation member and sends out the guide wire 70 from the distal end opening 15a of the inner needle 12. Subsequently, the user advances the catheter 30 and the catheter hub 50 along the guide wire 70 by advancing the catheter operation member 60. At this time, the sliding resistance between the inner needle 12 and the catheter is low because the gap 39 is formed between the inner needle 12 and the second inner peripheral surface 38 of the main lumen 34. As a result, the catheter 30 can be smoothly moved relative to the inner needle 12.

After the multi-structure needle 11 is somewhat inserted into the blood vessel, blood flows into the sub lumen 41 from the second lateral opening 41a. As a result, the user can satisfactorily recognize that the sub lumen 41 has secured the blood vessel as well.

Once the needle tip 13 of the inner needle 12 moves to the proximal end side beyond the second inner peripheral surface 38 of the catheter 30 in particular, it is possible to easily retract the inner needle 12 relative to the catheter 30. The catheter 30 and the catheter hub 50 are indwelled into the patient once the catheter 30 and the catheter hub 50 are sent out from the inner needle 12 and the housing 20. During the indwelling, an infusion tube is connected to each of the main hub 51 and the sub hub 52. As a result, a first drug is administered to the patient via the main space 51a and the main lumen 34 and a second drug is administered to the patient via the sub space 52a, the flow path 53, and the sub lumen 41.

As described above, in the catheter assembly 10 according to the first embodiment, while the first inner peripheral surface 36 on the distal end side of the main lumen 34 is in close contact with the outer peripheral surface 16 of the inner needle 12, the gap 39 is formed between the outer peripheral surface 16 of the inner needle 12 and the second inner peripheral surface 38, which is closer to the proximal end side than the first inner peripheral surface 36. Accordingly, at the position where the first inner peripheral surface 36 is formed, the catheter 30 is reliably supported by the inner needle 12 even if pressure is received from a biological tissue during puncturing, and thus deflection, shrinkage, and the like of the catheter 30 are suppressed. Accordingly, the distal end of the catheter 30 is smoothly inserted into the body. In addition, the gap 39 of the second inner peripheral surface 38 smoothens the relative movements of the inner needle 12 and the catheter 30 by suppressing the sliding resistance between the catheter 30 and the inner needle 12, and thus the operability of the catheter 30 during insertion and indwelling is improved. Further, a user can satisfactorily recognize blood vessel securing because the hole portion 14 is disposed. In other words, the catheter 30 having the plurality of lumens 31 can be easily inserted with the catheter assembly 10 and various treatments such as administration of a plurality of types of drugs and blood sampling can be carried out well with the catheter assembly 10.

The distal end side of the catheter 30 can be reduced in thickness in terms of outer shape and is more reliably supported by the inner needle 12 as the first inner peripheral surface 36 forms the close contact portion 35 with the inner needle 12. Accordingly, the insertion performance of the catheter 30 is significantly enhanced. In the catheter 30, the first outer peripheral surface 42 is thinner than the second outer peripheral surface 44, and thus the catheter 30 can be easily inserted into a blood vessel from the distal end. The tapered outer peripheral surface 43 is inserted subsequently to the first outer peripheral surface 42, and then the second outer peripheral surface 44 is inserted. Accordingly, the thick second outer peripheral surface 44 can be inserted with ease.

Further, in the catheter 30 having the soft tip 33, the soft tip 33 that is in contact with the wall of the blood vessel is easily deflected and curved along the blood vessel during insertion into the blood vessel, and thus inflammation or damage occurrence with respect to the blood vessel wall can be significantly reduced. Especially, the first inner peripheral surface 36 of the catheter 30 is supported by the inner needle 12, and thus the occurrence of deflection or shrinkage of the soft tip 33 can be effectively suppressed during the insertion that is performed before the blood vessel is reached.

In the catheter assembly 10, the second lateral opening 41a of the sub lumen 41 is positioned closer to the proximal end side than the hole portion 14. Accordingly, the vicinity of the distal end of the catheter 30 can be reduced in thickness and insertability improvement can be achieved. In addition, the blood that flows into the main lumen 34 can be quickly confirmed. The second lateral opening 41a of the sub lumen 41 is capable of suppressing mixing of drugs immediately when the plurality of types of drugs are administered to the blood vessel.

The catheter assembly 10 has the deflection suppression mechanism 90 (support member 91, holding portion of the catheter operation member 60) on the proximal end side that is beyond the second lateral opening 41a. As a result, it is possible to reduce the sliding resistance of the catheter 30 with respect to the deflection suppression mechanism 90 during advancement of the catheter 30. The deflection suppression mechanism 90 supports the catheter 30 on the proximal end side that is beyond the tapered outer peripheral surface 43 or the continuous inclined surface 45 of the catheter 30. As a result, the sliding resistance of the catheter 30 with respect to the deflection suppression mechanism during advancement of the catheter 30 can be further reduced. Further, deflection of the inner needle 12 can be prevented with a constant force by damage to the deflection suppression mechanism attributable to hitting against the second lateral opening 41a or the tapered outer peripheral surface 43 being prevented and a step attributable to the second lateral opening 41a or the tapered outer peripheral surface 43 being eliminated in the contact place and the planned contact place of the deflection suppression mechanism 90.

It should be noted that the present invention is not limited to the embodiment described above and various modifications can be made in line with the gist of the invention.

For example, an example in which the guide wire 70 is applied as an insertion assistance mechanism assisting with insertion of the catheter 30 has been described in the above embodiment. The insertion assistance mechanism is not limited thereto, and various configurations may be adopted as the insertion assistance mechanism. For example, the insertion assistance mechanism may be configured such that the guide wire 70 can be used in a retrofitted manner by exposure of the proximal end opening of the inner needle 12 from the inner needle hub 19. Further, the insertion assistance mechanism may be configured such that the guide wire 70 is automatically retractable into the hollow portion 12a after exposure from the needle tip 13. Alternatively, the catheter assembly 10 may be configured without the guide wire 70 and the guide wire operation member 80.

The insertion assistance mechanism may be configured such that the guide wire 70 extends at least twice with respect to the amount of operation of the guide wire operation member 80. For example, a configuration in which the guide wire 70 is folded back in the housing 20 and the guide wire operation member 80 advances and retracts the folded portion of the guide wire 70 may be adopted as this type of structure.

The catheter assembly 10 may be provided with a safety mechanism (not illustrated) for preventing erroneous puncturing with the inner needle 12 during removal of the inner needle 12. For example, applicable as the safety mechanism is a full cover-type mechanism causing a tubular member (such as a telescopic member) to protrude from the inner needle hub 19 during removal of the inner needle 12 and accommodating the inner needle 12 inside. In addition, the safety mechanism may be a covering member that partially covers the needle distal end 13 of the inner needle 12 and the periphery of the needle tip 13. Further, the safety mechanism may be a mechanism that automatically or manually pulls the inner needle 12 into the housing 20 (inner needle hub 19) during removal of the inner needle 12.

Alternatively, the safety mechanism may be configured to cause a blunt needle having a distal end with which the skin is hardly pierced to protrude from the needle tip 13 during removal of the inner needle 12. With the blunt needle configured to protrude from the needle tip 13 during advancement of the catheter with respect to the inner needle 12, piercing of the catheter with the inner needle 12 can be prevented as well.

The catheter assembly 10 may be provided with a hemostatic mechanism (not illustrated) preventing leakage of reverse blood from a patient. For example, a hemostatic valve accommodated in the catheter hub 50 can be an example of the hemostatic mechanism. In addition, the hemostatic valve may be a cap-type valve that is detachably attached to the proximal end of the catheter hub 50. Alternatively, the hemostatic mechanism may be a gas-permeable and liquid-impermeable air vent member attached to a predetermined position (such as the proximal end) of the inner needle 12.

The catheter assembly 10 may be provided with a catheter hub rotation mechanism (not illustrated) that allows the catheter hub to rotate with respect to the inner needle 12 in order to eliminate sticking of the catheter 30 to the inner needle 12 before puncturing with the multi-structure needle 11. For example, the catheter hub rotation mechanism can be configured by a notch being formed in at least one of the leftward and rightward directions of the position that corresponds to the sub hub 52 in the pre-puncture state and is in the axial direction of the housing 20 and the catheter operation member 60.

The catheter 30 may adopt various mechanisms in addition to the flexible mechanism that is based on the soft tip 33. For example, a rigid mechanism that prevents crushing of the catheter 30 can be applied by, for example, a blade or a ring-shaped, mesh-shaped, or coil-shaped reinforcing material being embedded in the catheter 30.

Further, a kink prevention mechanism (not illustrated) may be applied to the catheter assembly 10 so that the catheter 30 is prevented from kinking. A deformable configuration of the distal end part of the catheter hub 50 can be an example of the kink prevention mechanism.

In the present embodiment, the catheter assembly 10 is constituted by a separation mechanism (separate member) that separates the catheter hub 50 and the catheter operation member 60 when the catheter hub 50 is detached from the inner needle 12. Alternatively, the catheter assembly 10 may be a configuration (non-separation mechanism) with which the catheter hub 50 and the catheter operation member 60 cannot be separated and can be integrally indwelled.

In an alternative configuration, the first inner peripheral surface 36 defining the main lumen 34 may be smaller in diameter than the second inner peripheral surface 38, and a gap between the first inner peripheral surface 36 and the outer peripheral surface 16 of the inner needle 12 may not be zero (that is, the close contact portion 35 may not be formed). This is because the inner needle 12 is capable of satisfactorily supporting the catheter 30 under inward pressure during puncturing even in this configuration.

Other embodiments and other configuration examples of the present invention will be described with reference to FIGS. 3 to 18. In the following description, identical configurations or functionally identical configurations will be denoted by the same reference numerals so that detailed descriptions of the configurations can be omitted. It is a matter of course that the above-described mechanisms of the catheter assembly (insertion assistance mechanism, safety mechanism, hemostatic mechanism, catheter hub rotation mechanism, flexible mechanism, rigid mechanism, kink prevention mechanism, separation mechanism, and non-separation mechanism) can be appropriately adopted for the following embodiments and configuration examples.

Second Embodiment

Figure 3:
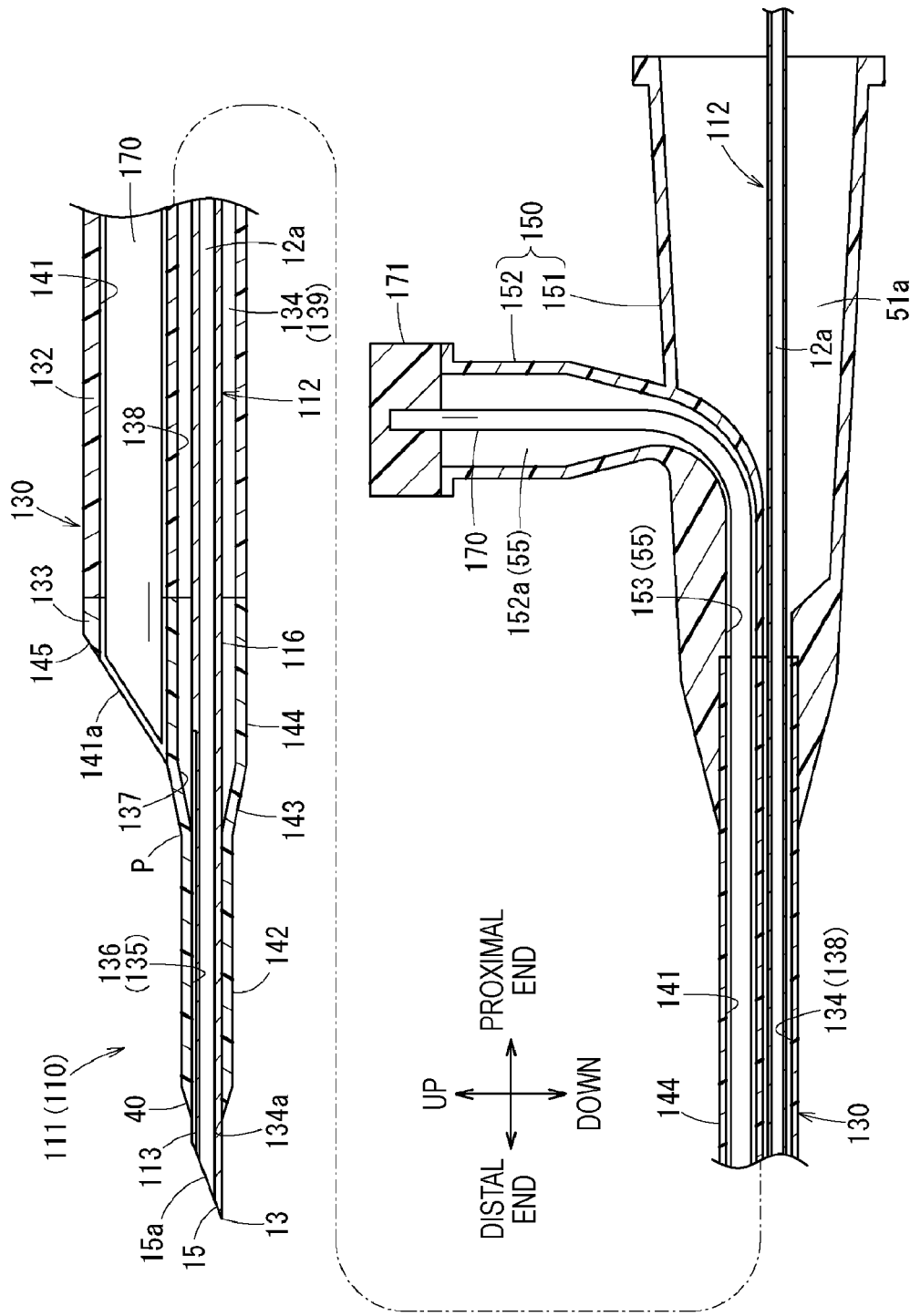
FIG. 3 is a side cross-sectional view illustrating a catheter, a catheter hub, and an inner needle of a catheter assembly according to a second embodiment.

As illustrated in FIG. 3, a catheter assembly 110 according to a second embodiment is different from the catheter assembly 10 according to the first embodiment in terms of the structure of a multi-structure needle 111 (inner needle 112 and catheter 130). Specifically, in the catheter 130, the diameter of a sub lumen 141 is larger than that of a main lumen 134 through which the inner needle 112 is inserted and disposed, and the inner needle 112 is formed so as to be thin correspondingly to the main lumen 134.

The inner needle 112 has a groove portion 113 as a blood flashback-realizing introduction path. The groove portion 113 is notched by a predetermined length from the blade surface 15 toward the proximal direction. The proximal end portion of the groove portion 113 communicates with a gap 139. An outer peripheral surface 116 of the inner needle 112 and the inner peripheral surface of the main lumen 134 (second inner peripheral surface 138) constitute the gap 139.

As in the first embodiment, the catheter 130 is constituted by a main body portion 132 and a soft tip 133 (flexible portion) provided at the distal end of the main body portion 132. However, the soft tip 133 is provided in the range from the distal end of the main lumen 134 to the proximal end side that is slightly beyond the distal end of the sub lumen 141 (second distal end opening 141a). A stylet 170 is disposed in the sub lumen 141.

The main lumen 134 of the catheter 130 is provided with a first inner peripheral surface 136 and the second inner peripheral surface 138. The diameter of the first inner peripheral surface 136 is almost equal to the outer diameter of the inner needle 112. The diameter of the second inner peripheral surface 138 is slightly larger than the outer diameter of the inner needle 112 including a tapered inner peripheral surface 137 (diameter of the first inner peripheral surface 136). The first inner peripheral surface 136 forms a close contact portion 135 between the first inner peripheral surface 136 and the outer peripheral surface 116 of the inner needle 112 other than the groove portion 113 (gap being zero). The gap 139 is formed between the second inner peripheral surface 138 and the outer peripheral surface 116 of the inner needle 112.

The sub lumen 141 is positioned in the direction that the blade surface 15 faces (upward direction). The sub lumen 141 extends (in parallel with the main lumen 134) along the axial direction of the catheter 130 and communicates with the second distal end opening 141a, which is positioned closer to the proximal end side than a first distal end opening 134a of the main lumen 134.

The outer peripheral surface of the catheter 130 has a first outer peripheral surface 142 at a position overlapping the first inner peripheral surface 136 and a second outer peripheral surface 144 having an outer diameter corresponding to the sub lumen 141 at a position overlapping the second inner peripheral surface 138. The distal end of the second outer peripheral surface 144 is continuous with an inclined end surface 145, which is inclined with respect to the axial center of the catheter 130. The second distal end opening 141a is formed in the inclined end surface 145 and the distal end of the inclined end surface 145 is continuous with the proximal end of a tapered outer peripheral surface 143.

The stylet 170 disposed in the sub lumen 141 is a solid rod-shaped member formed so as to be larger in diameter than the inner needle 112 and enhances the insertion performance of the catheter 130 for insertion into a living body by providing stiffness to the catheter 130 as a whole. The distal end of the stylet 170 is inclined to substantially the same extent as the inclined end surface 145 of the catheter 130. In the pre-puncture state, the distal end of the stylet 170 is disposed slightly closer to the proximal end side than the second distal end opening 141a. As a result, the distal end of the stylet 170 suppresses clogging of the sub lumen 141 with biological tissue pieces.

The stylet 170 extends in the sub lumen 141 and is inserted through a sub space 152a of a sub hub 152, which is connected to a main hub 151 (catheter hub 150), via a communication path 153 from the sub lumen 141. The proximal end of the stylet 170 is fixed and held by a stylet holding member 171 attached to the protruding end of the sub hub 152. Accordingly, with the catheter 130 somewhat inserted in a blood vessel, a user can remove the stylet 170 from the catheter 130 by gripping the stylet holding member 171.

An appropriate gap is provided between the outer surface of the stylet 170 and the inner surface of the sub lumen 141, and thus the stylet 170 can be slid with respect to the catheter 130. In addition, it can be seen that the distal end of the sub lumen 141 is inserted in a blood vessel by blood flowing into the gap between the stylet 170 and the sub lumen 141.

Although a cross section of the stylet 170 may have a shape in which the sub lumen 141 is reduced in a similar shape, the flashback can be confirmed better by means of groove installation. In addition, the stylet 170 may be made of a hollow transparent material. The flashback can be confirmed better by means of this configuration as well.

As described above, the catheter assembly 110 according to the second embodiment is capable of obtaining effects similar to those of the catheter assembly 10 according to the first embodiment. In other words, deflection or shrinkage of the catheter 130 is suppressed by the catheter 130 having a distal end supported by the outer peripheral surface 116 of the inner needle 112, and thus the catheter 130 can be smoothly inserted into the body. In a case where the inner needle 112 is formed so as to be thin in particular, a patient's wound can be reduced during puncturing with the inner needle 112 and hemostasis in the case of erroneous puncturing is facilitated.

As for the second distal end opening 141a of the sub lumen 141 facing the distal direction of the catheter 130, blocking by the wall of a blood vessel in a state of being indwelled in the blood vessel is suppressed. Accordingly, blood can be suctioned well from the second distal end opening 141a of the sub lumen 141. Further, in the catheter assembly 110, the stylet 170 is detachably disposed in the sub lumen 141, and thus the rigidity and the straightness of the catheter 130 can be improved by the stylet 170.

Third Embodiment

Figure 4:
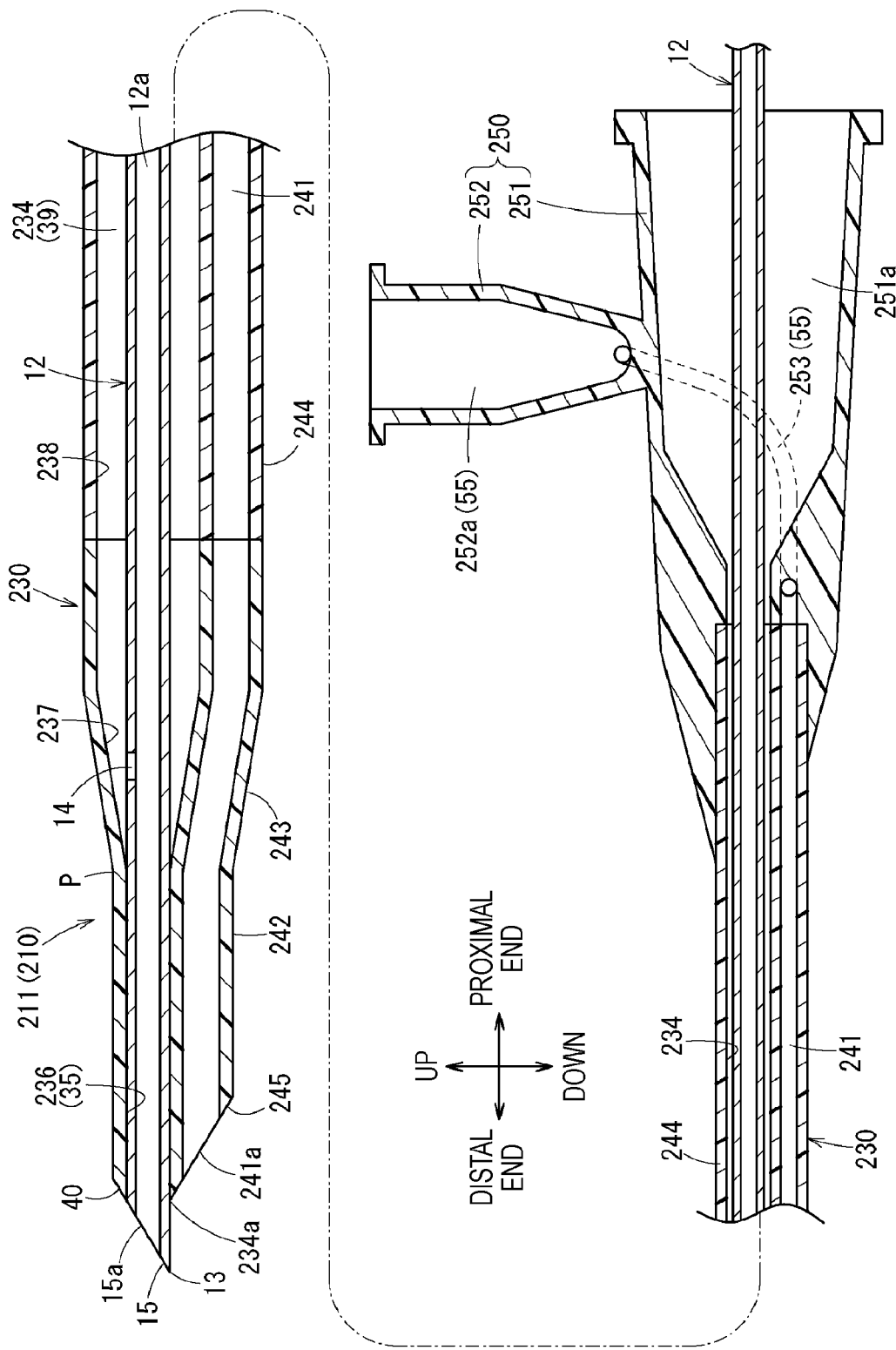
FIG. 4 is a side cross-sectional view illustrating a catheter, a catheter hub, and an inner needle of a catheter assembly according to a third embodiment.

As illustrated in FIG. 4, a catheter assembly 210 according to a third embodiment is different from the catheter assemblies and 110 according to the first and second embodiments in terms of the structures of a multi-structure needle 211 (catheter 230) and a catheter hub 250. Specifically, in a side cross-sectional view of the catheter 230, a main lumen 234 is provided on the upward direction side of a sub lumen 241 and the inner needle 12 is inserted through and disposed in the main lumen 234. In the third embodiment, the diameter of the main lumen 234 (second inner peripheral surface 238) is larger than that of the sub lumen 241. It should be noted that configurations similar to those of the second embodiment are adopted for the soft tip (flexible portion) and the main body portion constituting the catheter 230 and the soft tip is provided in the range from the distal end of the catheter 230 to a second outer peripheral surface 244.

As in the case of the main lumen 34 of the first embodiment, the main lumen 234 of the catheter 230 has the second inner peripheral surface 238 including a first inner peripheral surface 236 and a tapered inner peripheral surface 237. Although the outer peripheral surface of the catheter 230 has a first outer peripheral surface 242, a tapered outer peripheral surface 243, and the second outer peripheral surface 244, the sub lumen 241 extends from the second outer peripheral surface 244 to the range in which the tapered outer peripheral surface 243 and the first outer peripheral surface 242 are formed. The sub lumen 241 is provided in the downward direction on the side opposite to the direction that the blade surface 15 of the inner needle 12 faces. A second distal end opening 241a of the sub lumen 241 is disposed at substantially the same axial position as the first distal end opening 234a of the main lumen 234.

Accordingly, the lower portion side of the first distal end opening 234a at the distal end of the catheter 230 (side where the sub lumen 241 is formed) is formed on an inclined end surface 245 continuous with the distal end tapered portion 40 although the outer shape of the catheter 230 is thick as a whole. The inclined end surface 245 is inclined at an appropriate angle on the lower side of the blade surface 15 of the inner needle 12, and thus insertion of the distal end of the catheter 230 (first outer peripheral surface 242) is smoothened. The second distal end opening 241a is provided in the inclined end surface 245. Although not illustrated, insertion of the distal end of the catheter 230 can be smoothened in a more satisfactory manner by the inner diameter of the distal end portion of the sub lumen 241 being reduced.

A main hub 251 of the catheter hub 250 forms a first space 251a so as to communicate with the main lumen 234 in the upper portion of the catheter 230. The main hub 251 has a bypass communication path 253 that allows communication between the sub lumen 241 provided on the lower portion side of the catheter 230 and a second space 252a of a sub hub 252 connected to the upper portion side of the main hub 251. The bypass communication path 253 is provided so as to curve in the peripheral wall that surrounds the first space 251a of the main hub 251 and communicates with the second space 252a.

As described above, the catheter assembly 210 according to the third embodiment is capable of obtaining effects similar to those of the catheter assembly 10. With the catheter assembly 210 in particular, it is possible to quickly confirm that blood has flowed into the sub lumen 241. This is because the second distal end opening 241a of the sub lumen 241 is positioned closer to the distal end side than the hole portion 14 of the inner needle 12.

Fourth Embodiment

As illustrated in FIG. 5, a catheter assembly 310 according to a fourth embodiment is different from the catheter assemblies 110, and 210 according to the first to third embodiments in terms of the structures of a multi-structure needle 311 (catheter 330) and a catheter hub 350. Specifically, in a plan cross-sectional view of the catheter 330, a sub lumen 341 and a main lumen 334 extend in parallel to each other with the sub lumen 341 adjacent in the lateral direction of the main lumen 334 (rightward direction in FIG. 5). The guide wire 70 is slidably disposed in the sub lumen 341 while the inner needle 12 is inserted through and disposed in the main lumen 334.

In the fourth embodiment, the diameter of the main lumen 334 is larger than that of the sub lumen 341. Configurations similar to those of the second embodiment are adopted for the soft tip (flexible portion) and the main body portion constituting the catheter 330 and the soft tip is provided in the range from the distal end of the catheter 330 to a second outer peripheral surface 344.

As in the case of the main lumen 34 of the first embodiment, the main lumen 334 of the catheter 330 has a second inner peripheral surface 338 that includes a first inner peripheral surface 336 and a tapered inner peripheral surface 337 and communicates with a distal end opening 334a. The outer peripheral surface of the catheter 330 has a first outer peripheral surface 342, a tapered outer peripheral surface 343, and the second outer peripheral surface 344.

The sub lumen 341 is provided in the place where the second outer peripheral surface 344 is formed. The diameter of the sub lumen 341 is set to an appropriate dimension in accordance with the outer diameter of the guide wire 70. An inclined end surface 345 continuous with the tapered outer peripheral surface 343 is formed at the distal end of the second outer peripheral surface 344, and a second distal end opening 341a is formed in the inclined end surface 345.

The catheter hub 350 has a main hub 351 and a sub hub 352, and the sub hub 352 is connected to the side of the main hub 351. The main hub 351 has a first space 350a communicating with the main lumen 334 and a communication path 353 communicating with a second space 352a of the sub hub 352. In other words, the guide wire 70 is inserted so as to be slidable with respect to the sub lumen 341 via the second space 352a and the communication path 353.

As described above, the catheter assembly 310 according to the fourth embodiment is capable of obtaining effects similar to those of the catheter assembly 10. In the catheter assembly 310 in particular, the guide wire 70 is slidably disposed in the sub lumen 341, and thus the guide wire 70 reinforces the catheter 330 during insertion of the multi-structure needle 311 and the insertion performance of the catheter 330 can be enhanced. The guide wire 70 is capable of guiding insertion of the catheter 330 well by being inserted into a blood vessel from the sub lumen 341.

The catheter assemblies 10, 110, 210, and 310 and the following catheter assemblies 510, 610, 710, 810, 910, and 1010 are not particularly limited as to the disposition relationship between main and sub lumens. In other words, adoptable are all of the disposition relationships between a main lumen α and a sub lumen β in catheters 430A to 430F according to first to sixth configuration examples illustrated in FIGS. 6A to 6F.

Figure 6C:
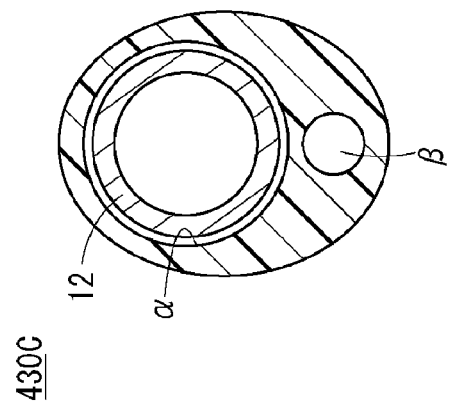
FIGS. 6A to 6F are cross-sectional views illustrating catheters and inner needles according to first to sixth configuration examples.
Figure 6B:
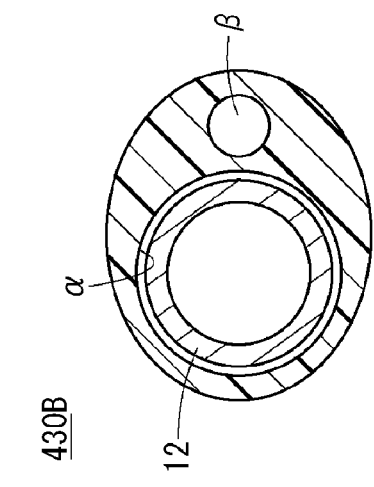
Figure 6A:
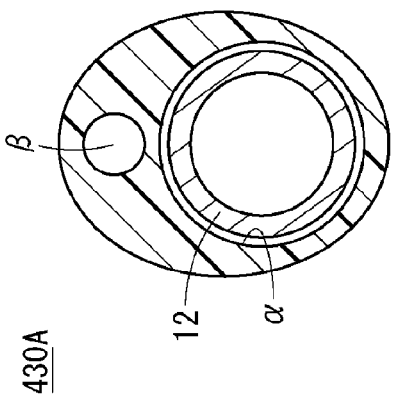
Figure 6F:
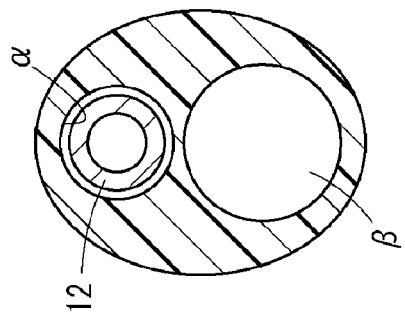
Figure 6E:
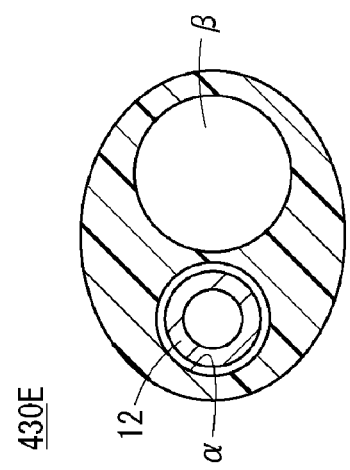

Specifically, the catheter 430A illustrated in FIG. 6A is the disposition relationship between the main lumen 34 and the sub lumen 41 described in the first embodiment. In other words, the diameter of the main lumen α is larger than that of the sub lumen β and the sub lumen β is disposed above the main lumen α. The cross-sectional shape of the catheter 430A that is orthogonal to the axial direction may be a shape other than the elliptical shape illustrated in FIG. 6A. Examples of the shape include the shape of a perfect circle. The same applies to the catheters 430B to 430F.

The positions of disposition of the main lumen α and the sub lumen β will be described based on the blade surface 15 of the inner needle 12 disposed in the main lumen α as an index. In other words and as described above, the blade surface 15 of the inner needle 12 is operated in terms of posture so as to face the upward direction in a case where the patient's body surface is the lower side during puncturing. Accordingly, the sub lumen β being present above the main lumen α means that the sub lumen β is positioned in the upward direction that the blade surface 15 faces and constitutes the circumferential direction of the catheter 430A.

The catheter 430A illustrated in FIG. 6A is capable of performing flashback confirmation by using the sub lumen β. In addition, suppressed in this catheter 430A is the place of formation of the distal end of the sub lumen β (inclined end surface) being caught by a blood vessel wall on the side opposite to the insertion place in a blood vessel and disturbed in terms of movement during blood vessel insertion. Accordingly, inflammation in or damage to the blood vessel wall can be suppressed as well. Furthermore, it is possible to suppress a decrease in flow rate attributable to the second distal end opening of the sub lumen β being closed by the blood vessel wall.

The catheter 430B illustrated in FIG. 6B is the disposition relationship between the main lumen 334 and the sub lumen 341 described in the fourth embodiment. In other words, the diameter of the main lumen α is larger than that of the sub lumen β and the sub lumen β is disposed in the lateral direction of the main lumen α that constitutes the circumferential direction of the catheter 430B (direction orthogonal to the direction that the blade surface faces). Effects similar to those of the disposition relationship illustrated in FIG. 6A can be obtained with this configuration. In addition, the flashback of the main lumen α can be confirmed well.

The catheter 430C illustrated in FIG. 6C is the disposition relationship between the main lumen 234 and the sub lumen 241 described in the third embodiment. In other words, the diameter of the main lumen α is larger than that of the sub lumen β and the sub lumen β is disposed below the main lumen α in the circumferential direction of the catheter 430C (direction opposite to the direction that the blade surface 15 faces). With this configuration, the flashback of the main lumen α can be confirmed better.

Figure 6D:
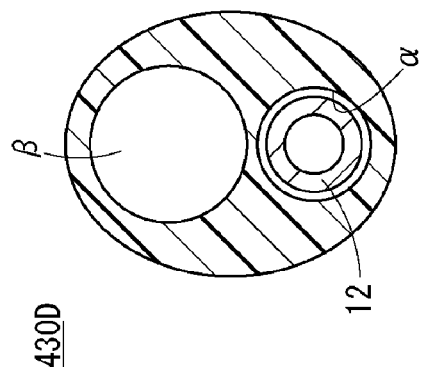

The catheter 430D illustrated in FIG. 6D is the disposition relationship between the main lumen 134 and the sub lumen 141 described in the second embodiment. In other words, the diameter of the sub lumen β is larger than that of the main lumen α and the sub lumen β is disposed above the main lumen α in the circumferential direction of the catheter 430D. In the 430E illustrated in FIG. 6E, the diameter of the sub lumen β is larger than that of the main lumen α and the sub lumen β is disposed in the lateral direction of the main lumen α. In the catheter 430F illustrated in FIG. 6F, the diameter of the sub lumen β is larger than that of the main lumen α and the sub lumen β is disposed below the main lumen α. Sufficient effects can be obtained, as in the case of the catheters 430A to 430C, with the catheters 430D to 430F illustrated in FIGS. 6D to 6F.

The cross-sectional shapes of the lumens are not particularly limited although the main lumen α and the sub lumen β have the shape of a perfect circle in cross section in FIGS. 6A to 6F. As an example, the lumen that is smaller in flow path cross-sectional area (such as the sub lumen) may have a shape (such as a C-shape, a U-shape, an elliptical shape, and a polygonal shape) surrounding a part of the circumferential outside of the main lumen α. Then, it is possible to reduce the outer diameters of all of the catheters 430A to 430F.

Figure 7A:
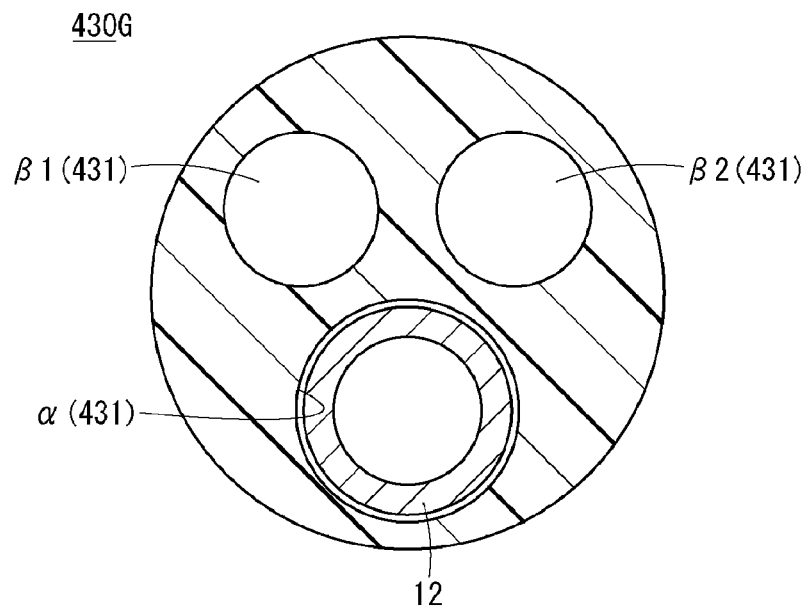
FIG. 7A is a cross-sectional view illustrating a catheter and an inner needle according to a seventh configuration example.
Figure 7B:
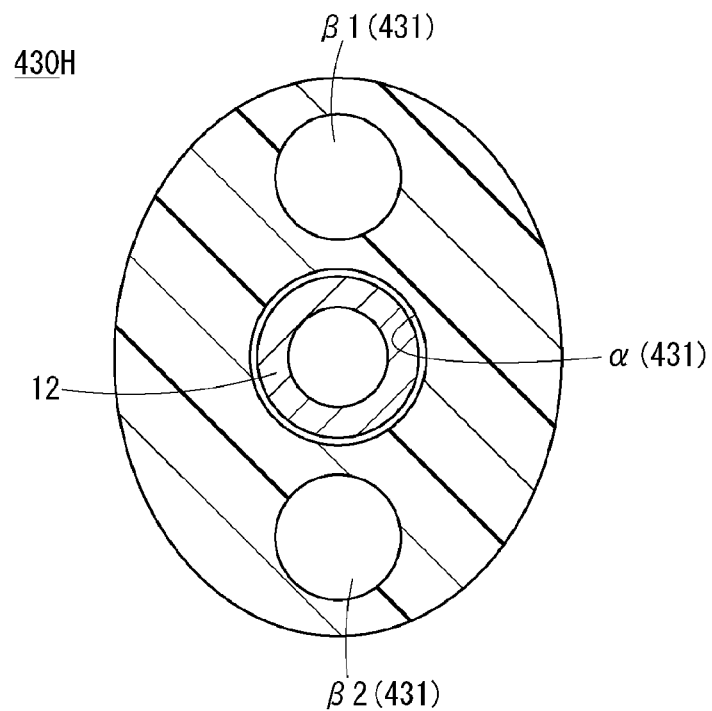
FIG. 7B is a cross-sectional view illustrating a catheter and an inner needle according to an eighth configuration example.

The catheter assembly may be configured to have three or more lumens 431 as in catheters 430G and 430H according to seventh and eighth configuration examples illustrated in FIGS. 7A and 7B. Specifically, in the catheter 430G illustrated in FIG. 7A, first and second sub lumens β1 and β2 are disposed above the main lumen α and side by side in the width direction (direction orthogonal to the direction that the blade surface 15 faces). In the catheter 430H illustrated in FIG. 7B, the main lumen α is disposed in the axial center portion of the catheter 430H, the first sub lumen β1 is disposed above the main lumen α (in the direction that the blade surface 15 faces), and the second sub lumen β2 is disposed below the main lumen α (in the direction opposite to the direction that the blade surface 15 faces).

The catheter assembly may be configured such that the flashback can be confirmed in the order of the main lumen α and the sub lumen β by the diameter and the length of each flashback flow path being appropriately set. Then, the flashback of the lumen that has a distal end opening portion can be confirmed first, and thus a user is unlikely to feel discomfort. Alternatively, the catheter assembly may be configured such that the flashback can be confirmed in the order of the sub lumen β and the main lumen a by the diameter and the length of each flashback flow path being appropriately set. Then, the catheter assembly can be used with ease on the part of a user who thinks that the main lumen α is naturally in a blood vessel with the sub lumen β in the blood vessel.

Fifth Embodiment

Figure 8:
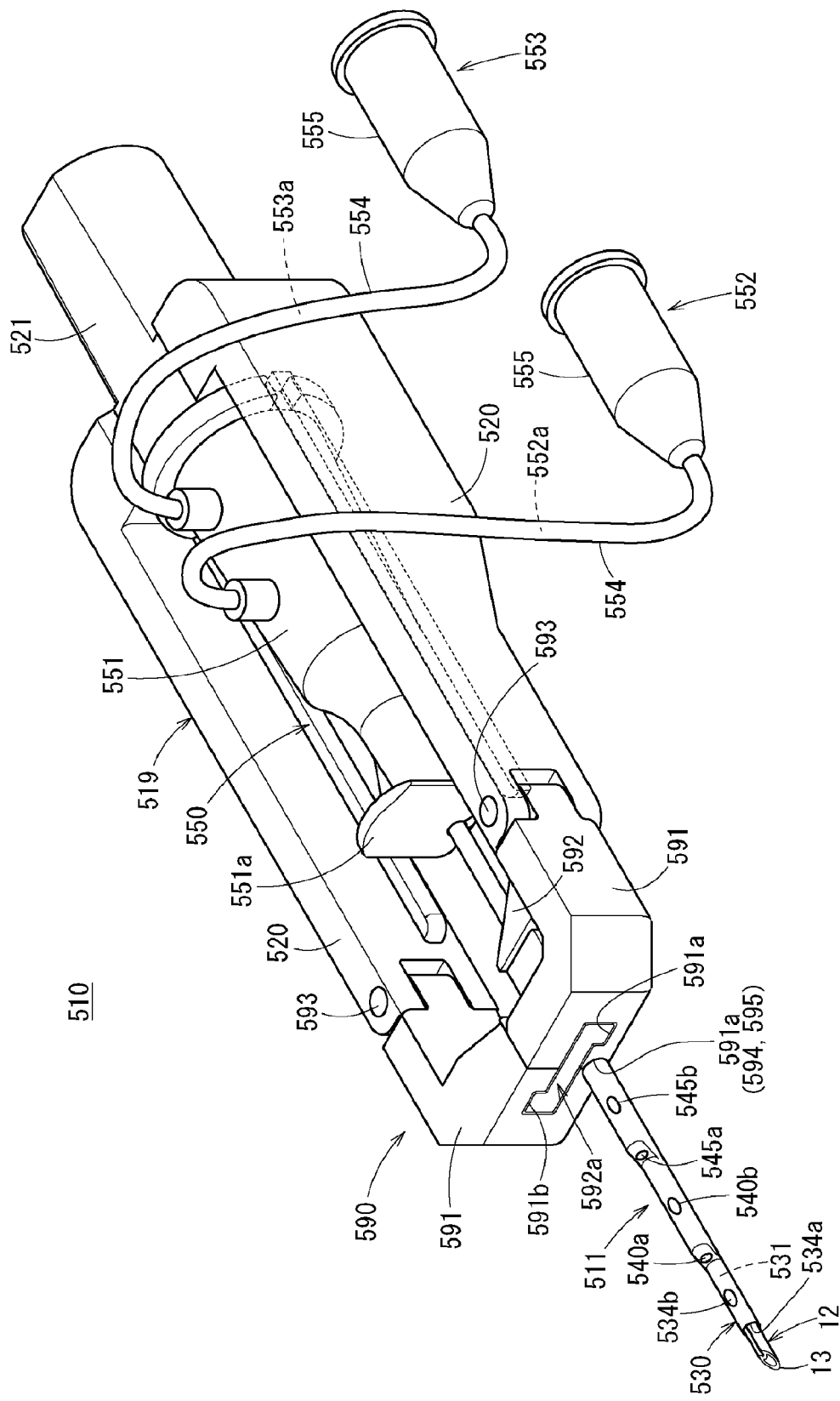
FIG. 8 is a perspective view illustrating an overall configuration of a catheter assembly according to a fifth embodiment.
Figure 9:
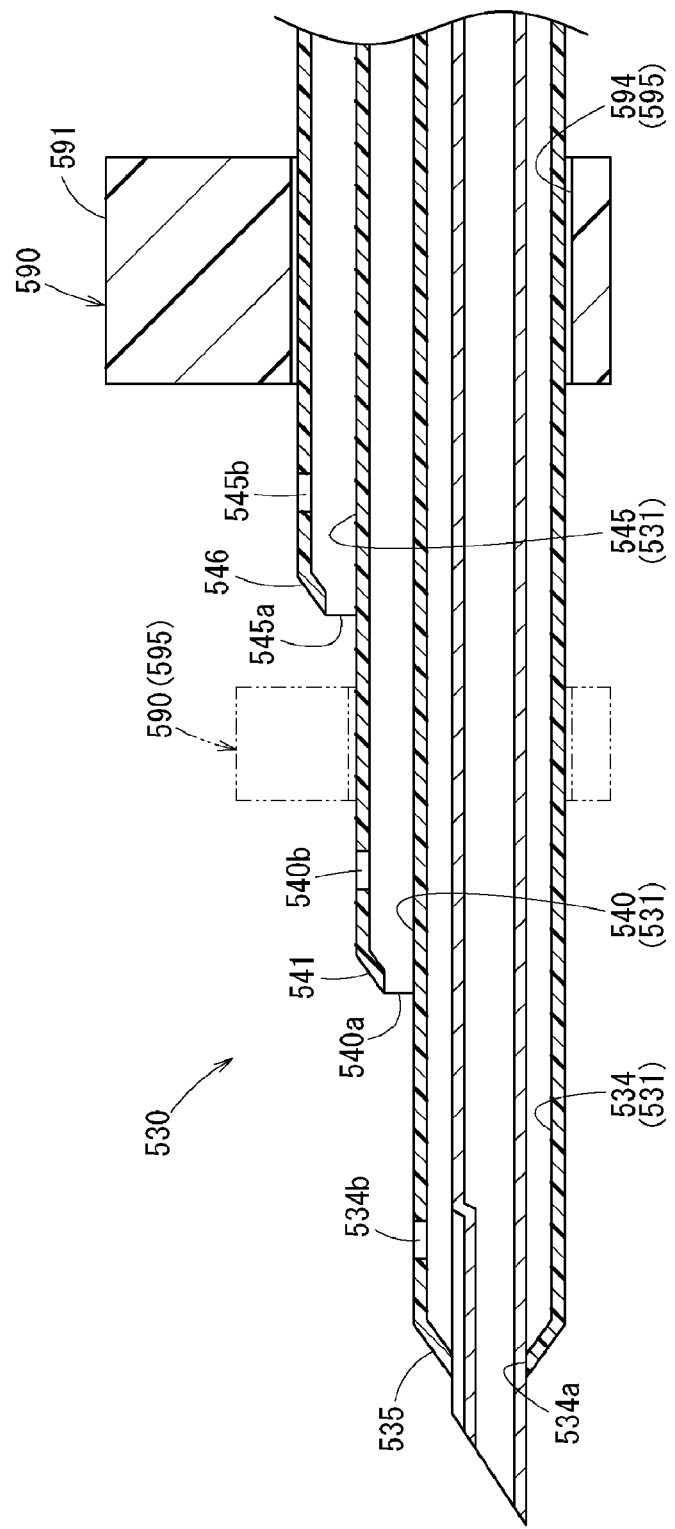
FIG. 9 is a side cross-sectional view illustrating a catheter, an inner needle, and a deflection suppression mechanism in FIG. 8.
Figure 10:
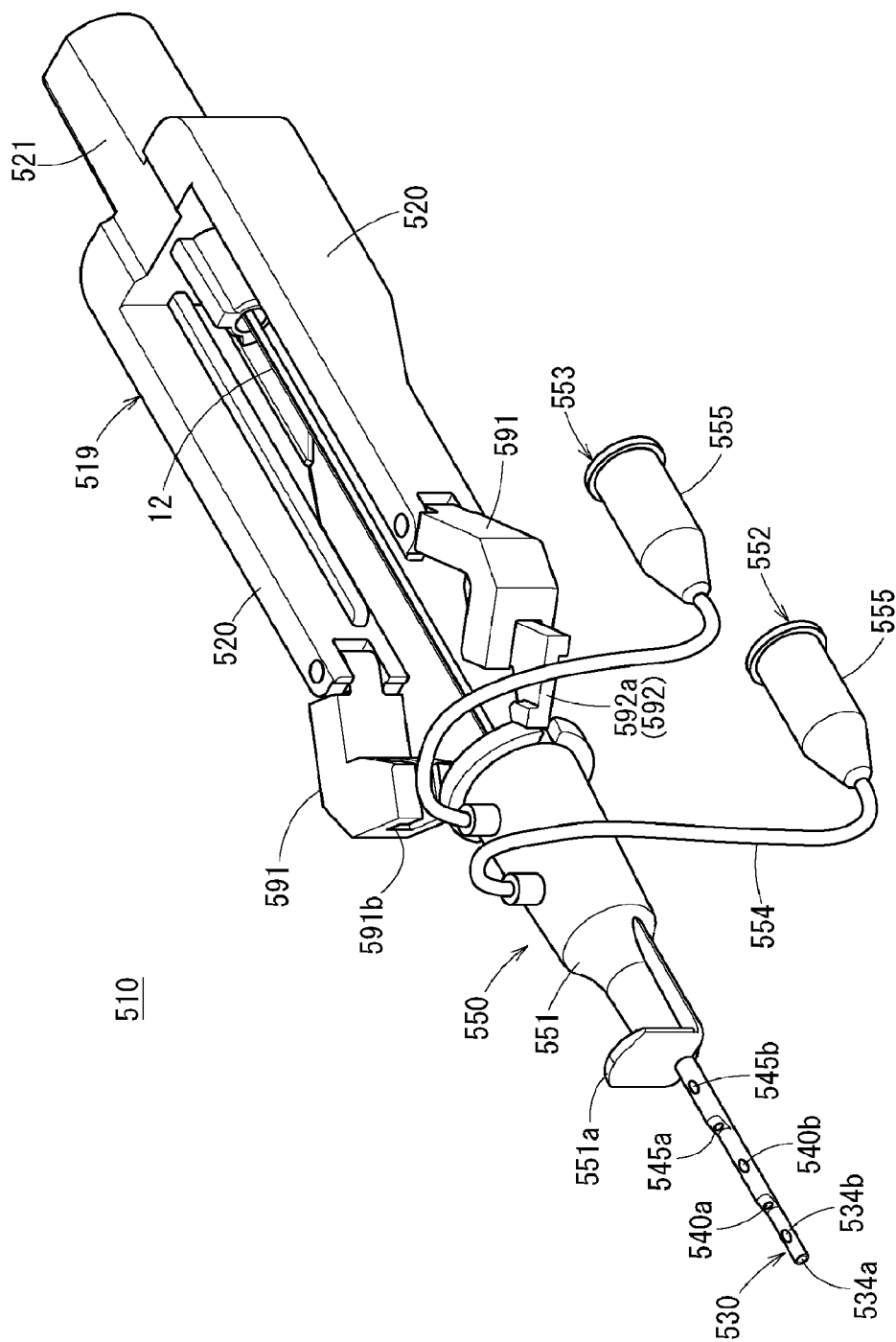
FIG. 10 is a perspective view illustrating operation of the catheter assembly in FIG. 8.

As illustrated in FIGS. 8 to 10, the catheter assembly 510 according to a fifth embodiment includes a catheter 530 having three lumens 531 as in the case of the seventh and eighth configuration examples and is configured such that a multi-structure needle 511 can be supported by a deflection suppression mechanism 590 of an inner needle hub 519. Specifically, in a side cross-sectional view along the axial direction, the catheter 530 has a main lumen 534 disposed on the lower side, an intermediately disposed first sub lumen 540, and a second sub lumen 545 disposed on the upper side.

The inner needle hub 519 of the catheter assembly 510 has a pair of extending portions 520 bifurcating from a base portion 521, which is at the center in the width direction. The inner needle hub 519 holds a catheter hub 550 in a state of upward and downward exposure. It should be noted that the inner needle hub 519 may have the shape of a housing with the lower and upper sides of the pair of extending portions 520 covered. In a case where the upper side is covered, the upper cover may be provided with a slit so that a tab can be exposed from the housing and operated.

The deflection suppression mechanism 590 has a pair of openable and closable support arms 591 and a restraining portion 592 that is capable of restraining the pair of support arms 591 in a closed state and is capable of releasing the restraint. The pair of support arms 591 are pivotally supported by a pair of support pins 593 and can be opened and closed in the leftward-rightward direction with respect to the pair of extending portions 520 of the inner needle hub 519.

Each support arm 591 is provided with a support groove 591a for holding the inner needle 12 in the closed state. The pair of support grooves 591a constitute a support hole 594 supporting the multi-structure needle 511. In the initial state of the catheter assembly 510, the wall surface that constitutes the support hole 594 functions as a sliding contact support portion 595 rubbing against the catheter 530 when the catheter 530 advances with respect to the inner needle 12. In the pre-puncture state, a slight gap is formed between the outer surface of the catheter 530 and the inner surface of the sliding contact support portion 595. In addition, the sliding contact support portion 595 surrounds the entire circumferential direction of the catheter 530 contactably.

Each support arm 591 is provided with a bent engagement groove 591b in a front view in the closed state. The restraining portion 592 has a head portion 592a corresponding to the shape in which the pair of engagement grooves 591b are continuous. In the pre-puncture state, the restraining portion 592 closes each support arm 591 by mutual engagement. The restraint with respect to the pair of support arms 591 is released by the pressing against the catheter hub 550 resulting from the advancement of the catheter hub 550.

The main lumen 534, the first sub lumen 540, and the second sub lumen 545 extend in parallel to one another in the catheter 530. The main lumen 534, the first sub lumen 540, and the second sub lumen 545 overlap each other in steps on the distal end side of the catheter 530.

Specifically, the main lumen 534 is formed so as to be longer than the first and second sub lumens 540 and 545 and communicates with a first distal end opening 534a (main opening) at the most distal end of the catheter 530 and the first proximal end opening (not illustrated) at the most proximal end of the catheter 530. The catheter 530 has a first tapered outer peripheral surface 535, which has an outer diameter gradually decreasing toward the first distal end opening 534a. A first lateral opening 534b (main opening) communicating with the main lumen 534 is provided at the midway position of the catheter 530 (between the first tapered outer peripheral surface 535 and a second distal end opening 540a to be described later).

The first sub lumen 540 is formed so as to be shorter than the main lumen 534 and longer than the second sub lumen 545. Here, the distal end side of the catheter 530 is increased in thickness (outer diameter) by the first sub lumen 540 overlapping the main lumen 534 and a second tapered outer peripheral surface 541 (tapered portion) constituting a step portion is provided at the most distal end of the first sub lumen 540. The first sub lumen 540 communicates with the second distal end opening 540a (sub opening) formed in the second tapered outer peripheral surface 541. The first sub lumen 540 communicates with the second proximal end opening (not illustrated) at the most proximal end of the catheter 530 (positioned coaxially with the first proximal end opening). A second lateral opening 540b (sub opening) communicating with the first sub lumen 540 is provided between the second tapered outer peripheral surface 541 of the catheter 530 and a third distal end opening 545a, which will be described later.

The second sub lumen 545 is formed so as to be shortest. The distal end side of the catheter 530 is further increased in thickness (outer diameter) by the second sub lumen 545 overlapping the main lumen 534 and the first sub lumen 540 and a third tapered outer peripheral surface 546 (tapered portion) constituting a step portion is provided at the most distal end of the second sub lumen 545. The second sub lumen 545 communicates with the third distal end opening 545a (sub opening) formed in the third tapered outer peripheral surface 546. The second sub lumen 545 communicates with the third proximal end opening (not illustrated) at the most proximal end of the catheter 530 (positioned coaxially with the first proximal end opening). A third lateral opening 545b (sub opening) communicating with the second sub lumen 545 is provided on the proximal end side of the third tapered outer peripheral surface 546 of the catheter 530.

The first lateral opening 534b and the second distal end opening 540a are set at positions that are apart from each other at a distance of 17 mm or more. Likewise, the second lateral opening 540b and the third distal end opening 545a are set at positions that are apart from each other at a distance of 17 mm or more.

In the present embodiment, the sliding contact support portion 595 of the deflection suppression mechanism 590 is positioned closer to the proximal end side than the third lateral opening 545b of the catheter 530 in the pre-puncture state. More specifically, the sliding contact support portion 595 is provided so as to be capable of supporting a position in the vicinity of the third lateral opening 545b (at a distance of, for example, 5 mm or less on the proximal end side), which is the sub opening of the two sub lumens 540 and 545 that is on the most proximal end side.

In the initial state of the catheter assembly 510, the sliding contact support portion 595 may be provided closer to the distal end side than the third distal end opening 545a of the second sub lumen 545 (see the two-dot chain line in FIG. 9). Specifically, the sliding contact support portion 595 is capable of supporting the proximal end side that is beyond the second distal end opening 540a (sub opening of the two sub lumens 540 and 545 that is on the most distal end side). Damage to the second tapered outer peripheral surface 541 and the second distal end opening 540a of the first sub lumen 540 and the like can be suppressed also with the above-described configuration in which the deflection suppression mechanism 590 supports the distal end side that is beyond the third distal end opening 545a. In addition, the deflection suppression effect of the inner needle 12 is improved.

The catheter hub 550 of the catheter assembly 510 has a main hub 551 functioning as a port of the main lumen 534. In addition, the catheter hub 550 has a first sub port 552 functioning as a port of the first sub lumen 540 and a second sub port 553 functioning as a port of the second sub lumen 545. A hub operation portion 551a, on which a user puts his or her finger, is provided at the distal end of the main hub 551. The hub operation portion 551a has a surface pushing out the restraining portion 592. The hub operation portion 551a may be configured so as to be removable from the main hub 551.

Each of the first and second sub ports 552 and 553 has a connecting part for the main hub 551, a soft flexible tube 554 (soft portion) fixed to the connecting part, and a sub hub 555 continuous with the proximal end of the flexible tube 554. The sub hub 555 is configured as a connector to which a medical device is connected. A first communication path 552a communicating with the first sub lumen 540 is formed in the first sub port 552 (main hub 551, flexible tube 554, and sub hub 555). Likewise, a second communication path 553a communicating with the second sub lumen 545 is formed in the second sub port 553.

The catheter assembly 510 according to the fifth embodiment is basically configured as described above. As for the catheter assembly 510, the deflection suppression mechanism 590 provides support in the vicinity of the proximal end of the third lateral opening 545b during puncturing with the multi-structure needle 511. Accordingly, puncturing with the multi-structure needle 511 can be performed with deflection of the inner needle 12 suppressed well.

As illustrated in FIG. 10, after puncturing with the multi-structure needle 511, a user advances the catheter 530 relative to the inner needle 12 by advancing the catheter hub 550. The catheter 530 can be smoothly advanced, without being caught, at this time because the deflection suppression mechanism 590 supports the proximal end side of the third lateral opening 545b of the second sub lumen 545. In addition, the catheter hub 550 pushes out the restraining portion 592 during the advancement, and thus the pair of support arms 591 are opened in the leftward-rightward direction. As a result, the support of the multi-structure needle 511 by the deflection suppression mechanism 590 can be released with ease and the catheter 530 and the catheter hub 550 can be detached from the inner needle 12.

As described above, the catheter assembly 510 is capable of obtaining effects similar to those of the catheter assembly 10. For example, the catheter assembly 510 is capable of easily supplying a liquid medicine or blood to the main lumen 534 and the first and second sub lumens 540 and 545 by a medical device being connected to the main hub 551 and the sub hub 555 during indwelling of the catheter 530. After the catheter 530 is indwelled, different types of liquid medicines are allowed to flow well and be administered into a blood vessel by the main lumen 534 and the first and second sub lumens 540 and 545 extending in parallel to each other.

The deflection suppression mechanism 590 supports the proximal end side of the second distal end opening 540a (sub opening at the most distal end) even in the configuration in which the catheter assembly 510 has a plurality of lumens, that is, the main lumen 534 and the first and second sub lumens 540 and 545. As a result, damage to the catheter 530 can be reduced and deflection of the inner needle 12 can be suppressed at the same time.

It is preferable that the deflection suppression mechanism 590 supports a place close to the needle tip 13 of the inner needle 12 for deflection of the inner needle 12 to be suppressed. For example, with the deflection suppression mechanism 590 configured to support the distal end side that is beyond the plurality of sub openings, the possibility of damage to the catheter 530 attributable to contact with the sub opening during a movement of the catheter 530 increases. In contrast to this, in the catheter assembly 510 according to the present embodiment, the position of formation of the sub opening and the support position of the deflection suppression mechanism 590 are appropriately disposed, and thus both deflection prevention for the inner needle 12 and catheter mobility can be achieved.

In the catheter assembly 510, the deflection suppression mechanism 590 supports the proximal end side that is beyond the third lateral opening 545b (sub opening on the most proximal end side), and thus damage to the catheter 530 can be prevented in a more reliable manner. Further, because the deflection suppression mechanism 590 supports the proximal end side that is beyond the third tapered outer peripheral surface 546, it is possible to prevent the deflection suppression mechanism 590 from being caught by the third tapered outer peripheral surface 546. Accordingly, the mobility of the catheter 530 can be further enhanced.

In the catheter assembly 510, the sub openings include the second and third lateral openings 540b and 545b. Accordingly, the liquid medicine or blood that has flowed in the first and second sub lumens 540 and 545 can be discharged well into a blood vessel. In addition, damage to the vicinity of the third lateral opening 545b is suppressed because the deflection suppression mechanism 590 is positioned on the proximal end side that is beyond the third lateral opening 545b.

In the catheter assembly 510, the first distal end opening 534a and the second distal end opening 540a are apart from each other at a distance of 17 mm or more. Accordingly, the liquid medicines flowing out from the first distal end opening 534a and the second distal end opening 540a can be mixed in a blood vessel. In other words, combination contraindications can be administered well with the single catheter 530.

In the catheter assembly 510, the deflection suppression mechanism 590 is capable of supporting the position at a distance of 5 mm or less on the proximal end side of the third lateral opening 545b. Accordingly, the distance from the needle tip 13 of the inner needle 12 to the deflection suppression mechanism 590 is shortened. Accordingly, deflection of the inner needle 12 can be suppressed with more firmness.

In the catheter assembly 510, the deflection suppression mechanism 590 surrounding the entire circumferential direction of the catheter 530 is capable of reliably suppressing upward, downward, leftward, and rightward shaking of the inner needle 12 (such as deviation from the deflection suppression mechanism 590 and deflection of the inner needle 12).

The catheter assembly 510 is provided with the first and second sub ports 552 and 553 including the sub hub 555 and the flexible tube 554, and thus the sub hub 555 can be freely placed in terms of position and posture. Accordingly, a user can satisfactorily carry out puncturing with the multi-structure needle 511 and insertion of the catheter 530.

It should be noted that the main opening that the main lumen 534 communicates with and the sub opening that the first and second sub lumens 540 and 545 communicate with are not limited to the configurations described above (first distal end opening 534a, first lateral opening 534b, second distal end opening 540a, second lateral opening 540b, third distal end opening 545a, third lateral opening 545b) and various configurations are adoptable instead. For example, the first distal end opening 534a may constitute the main opening alone.

The sub opening of the first sub lumen 540 may be only one of the second distal end opening 540a and the second lateral opening 540b. Likewise, the sub opening of the second sub lumen 545 may be only one of the third distal end opening 545a and the third lateral opening 545b.

In a case where the second lateral opening 540b constitutes the sub opening of the first sub lumen 540 alone and the third lateral opening 545b constitutes the sub opening of the second sub lumen 545 alone, for example, the second tapered outer peripheral surface 541 and the third tapered outer peripheral surface 546 constitute a step portion of the catheter 530 that is blocked. In this configuration, the deflection suppression mechanism 590 may provide support in the vicinity of the proximal end of the second tapered outer peripheral surface 541 or the third tapered outer peripheral surface 546. Even with this configuration, it is possible to satisfactorily avoid catching of the deflection suppression mechanism 590 with respect to the second tapered outer peripheral surface 541 or the third tapered outer peripheral surface 546.

Various configurations can be adopted for the deflection suppression mechanism 590. For example, the inner surface of the support hole 594 constituting the sliding contact support portion 595 may be formed in a tapered shape so as to be tapered toward the distal direction. Then, it is possible to reduce catching of the third tapered outer peripheral surface 546 with respect to the sliding contact support portion 595 even with a configuration having a tapered portion (such as the third tapered outer peripheral surface 546) as in the case of the catheter 530 and having the sliding contact support portion 595 on the distal end side.

It is a matter of course that the configuration of the deflection suppression mechanism 590 and the configuration of the sub lumen (including the tapered portion) in the catheter 530 are applicable to the following embodiments.

Sixth Embodiment

Figure 11:
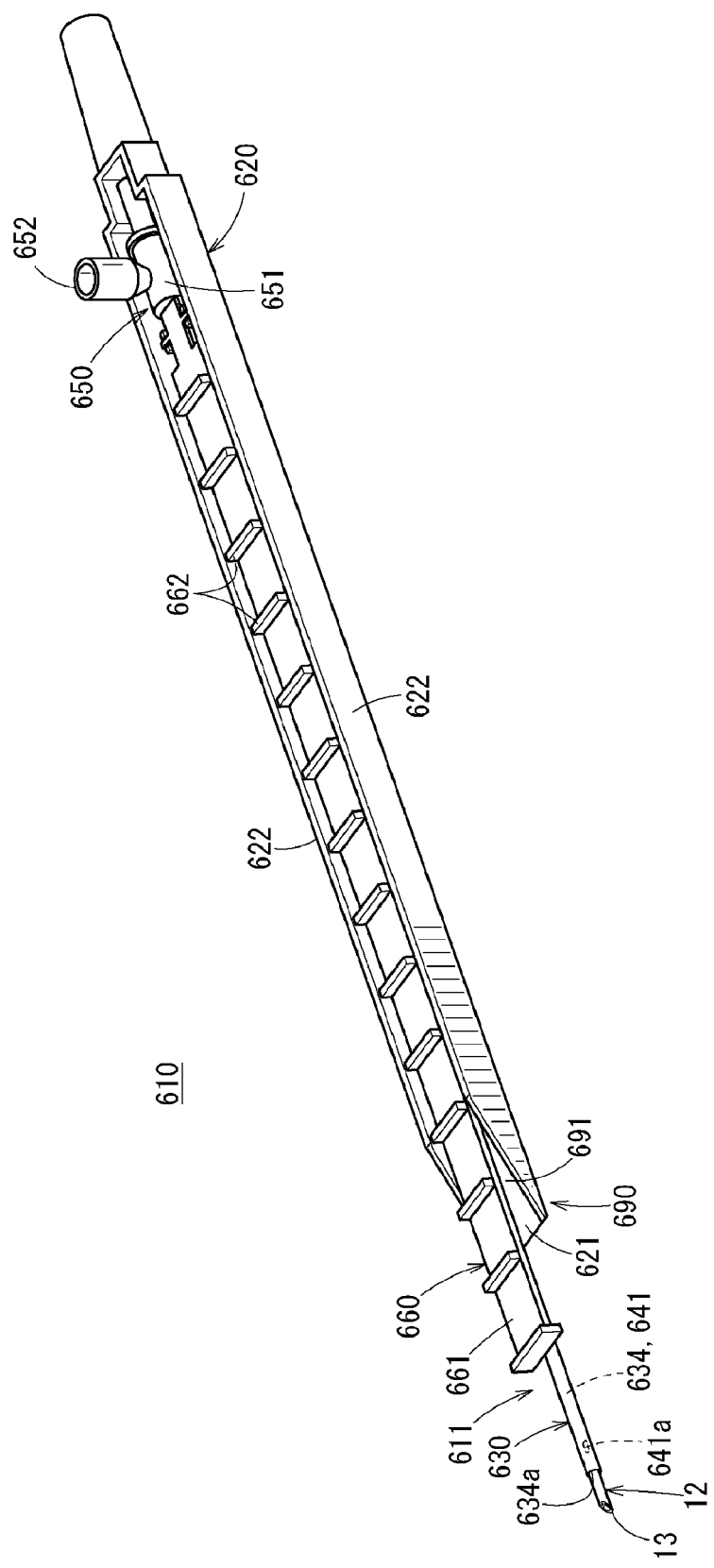
FIG. 11 is a perspective view illustrating an overall configuration of a catheter assembly according to a sixth embodiment.
Figure 12A:
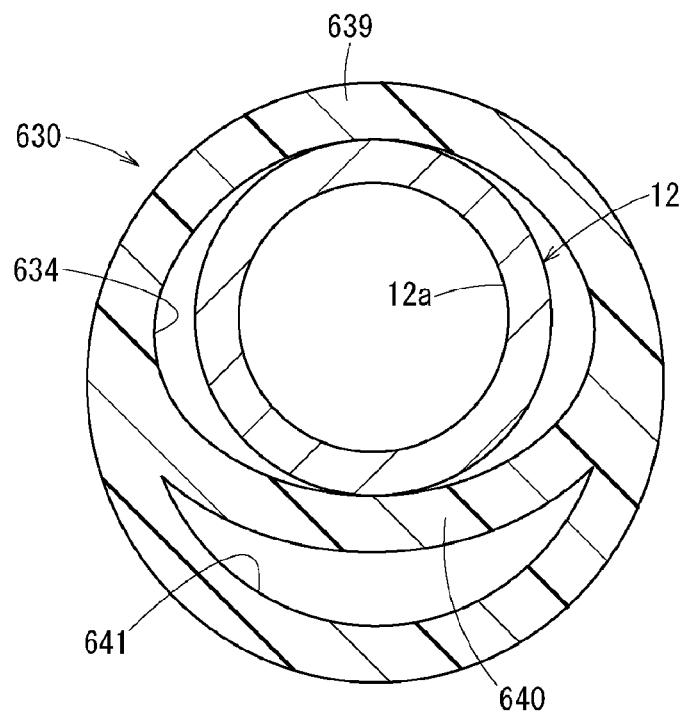
FIG. 12A is a cross-sectional view illustrating a multi-tube structure in FIG. 11.
Figure 12B:
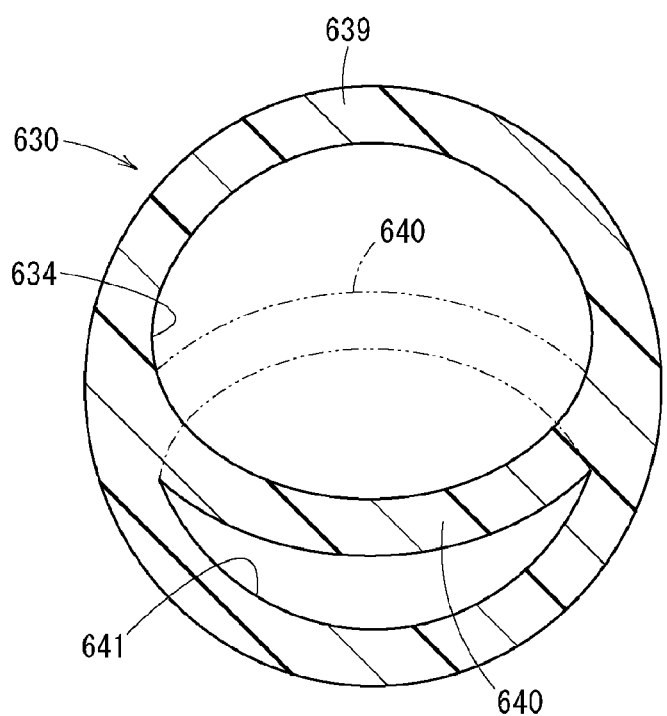
FIG. 12B is a cross-sectional view illustrating operation during a catheter-based liquid flow.

As illustrated in FIGS. 11, 12A, and 12B, a catheter 630 of the catheter assembly 610 according to a sixth embodiment is configured such that a main lumen 634 and a sub lumen 641 are disposed in the upward-downward direction and the two lumens are partitioned by a partition wall 640. The partition wall 640 is configured to be deformable in response to the pressure of the main lumen 634 and the sub lumen 641.

Specifically, the main lumen 634 of the catheter 630 communicates with a distal end opening 634a formed at the distal end of the catheter 630 and communicates with the proximal end opening (not illustrated) formed at the proximal end of the catheter 630. In the pre-puncture state, the inner needle 12 is detachably disposed in the main lumen 634.

The sub lumen 641 of the catheter 630 is positioned below the main lumen 634 and extends in parallel with the main lumen 634. The sub lumen 641 communicates with a lateral opening 641a, which is formed at the midway position on the lower side of the catheter 630.

The partition wall 640 extends along the axial direction of the catheter 630 and separates the main lumen 634 and the sub lumen 641 from each other. Although the partition wall 640 is connected at a position shifted in phase by approximately 180° with respect to a tubular wall portion 639 of the catheter 630 in a cross-sectional view orthogonal to the axial direction of the catheter 630, the partition wall 640 has a length exceeding the diameter of the tubular wall portion 639 (has a margin). The partition wall 640 is configured so as to be more flexible than the tubular wall portion 639 and can be deformed by receiving a predetermined positive pressure or more pressure from a liquid medicine.

As illustrated in FIG. 12A, for example, the partition wall 640 is capable of spreading downward and allowing the inner needle 12 to be disposed well in a state where the inner needle 12 is inserted through the main lumen 634. As illustrated in FIG. 12B, for example, the partition wall 640 increases the flow path cross-sectional area of the main lumen 634 in a case where a liquid medicine is allowed to flow in quantity through the main lumen 634. In a case where a liquid medicine is allowed to flow in quantity through the sub lumen 641, the partition wall 640 increases the flow path cross-sectional area of the sub lumen 641 as indicated by the two-dot chain line in the illustrated example.

Returning to FIG. 11, the catheter assembly 610 fixes and holds the proximal end of the catheter 630 by means of a catheter hub 650. The catheter hub 650 has a sub hub 652 protruding upward from a main hub 651 as in the first embodiment.

A catheter operation member 660 is a long plate corresponding to the elongated inner needle 12 and the catheter 630 (multi-structure needle 611). The catheter operation member 660 is fixed so as to be rotatable with respect to the catheter hub 650. The catheter operation member 660 has a pressing portion 661 capable of pressing the part between the proximal end and the distal end of the catheter 630. The pressing portion 661 constitutes a part of a deflection suppression mechanism 690. The catheter operation member 660 has a plurality of non-slip ribs 662, which are spaced apart from one another on the upper surface of the catheter operation member 660.

A housing 620 of the catheter assembly 610 is formed in an elongated bowl shape, accommodates the proximal end side of the multi-structure needle 611, and movably accommodates the catheter hub 650. The housing 620 has a bottom plate 621 and left and right side walls 622 extending upward from the left and right sides of the bottom plate. The housing 620 is open upward and to the distal end side. The distal end portion of the bottom plate 621 is a sliding contact support portion 691 rubbing against the catheter 630 when the catheter 630 advances with respect to the inner needle 12.

The sliding contact support portion 691 and the pressing portion 661 constitute the deflection suppression mechanism 690. The deflection suppression mechanism 690 is capable of supporting the inner needle 12 and the catheter 630 (multi-structure needle 611) between the sliding contact support portion 691 and the pressing portion 661 when the catheter 630 advances with respect to the inner needle 12. In the pre-puncture state, the sliding contact support portion 691 is disposed at a position where the proximal end side that is beyond the lateral opening 641a of the catheter 630 can be supported.

The catheter assembly 610 according to the sixth embodiment is basically configured as described above. In using the catheter assembly 610, a user performs puncturing by pressing the distal end portion of the catheter assembly 610 (distal end portion of the catheter 630 through which the inner needle 12 is inserted) against a patient while pressing the distal end portion of the catheter operation member 660 with the index finger of one hand. The catheter 630 is sandwiched and supported between the pressing portion 661 and the distal end portion (sliding contact support portion 691) of the housing 620 in a state where the midway part of the catheter 630 is pressed with the catheter operation member 660 (pressing portion 661). As a result, deflection of the multi-structure needle 611 is suppressed.

Then, the distal end of the catheter 630 is inserted to a target position in a blood vessel by the catheter operation member 660 being advanced relative to the inner needle 12 and the housing 620. When the catheter 630 moves in the distal direction with respect to the inner needle 12, the catheter 630 slides with respect to the sliding contact support portion 691. Subsequently, the housing 620 is pulled in the proximal direction while the catheter operation member 660 is pressed with the other hand. As a result, the catheter 630 and the catheter hub 650 can be indwelled in the patient by detachment of the inner needle 12 from the catheter hub 650 and removal of the catheter operation member 660.

The catheter assembly 610 is capable of obtaining effects similar to those of the other embodiments described above. In other words, the deflection suppression mechanism 690 supports a position (proximal end position at a distance of, for example, 5 mm or less) in the vicinity of the proximal end side of the lateral opening 641a of the sub lumen 641 (sub opening at the most distal end). As a result, damage to the catheter 630 can be reduced and deflection of the inner needle 12 can be suppressed at the same time.

In the catheter assembly 610 in particular, the main lumen 634 and the sub lumen 641 are partitioned from each other by the partition wall 640, which can be deformed in response to pressure. Accordingly, in the pre-puncture state, the relative movements of the catheter 630 and the inner needle 12 can be simplified by the main lumen 634 being enlarged. During drug or blood administration, the partition wall 640 is appropriately deformed by the fluid pressure resulting from the administration. For example, a flow path cross-sectional area can be ensured with ease even in a case where the liquid medicine of the sub lumen 641 is caused to flow by a relatively larger amount than the liquid medicine of the main lumen 634.

Seventh Embodiment

Figure 13:
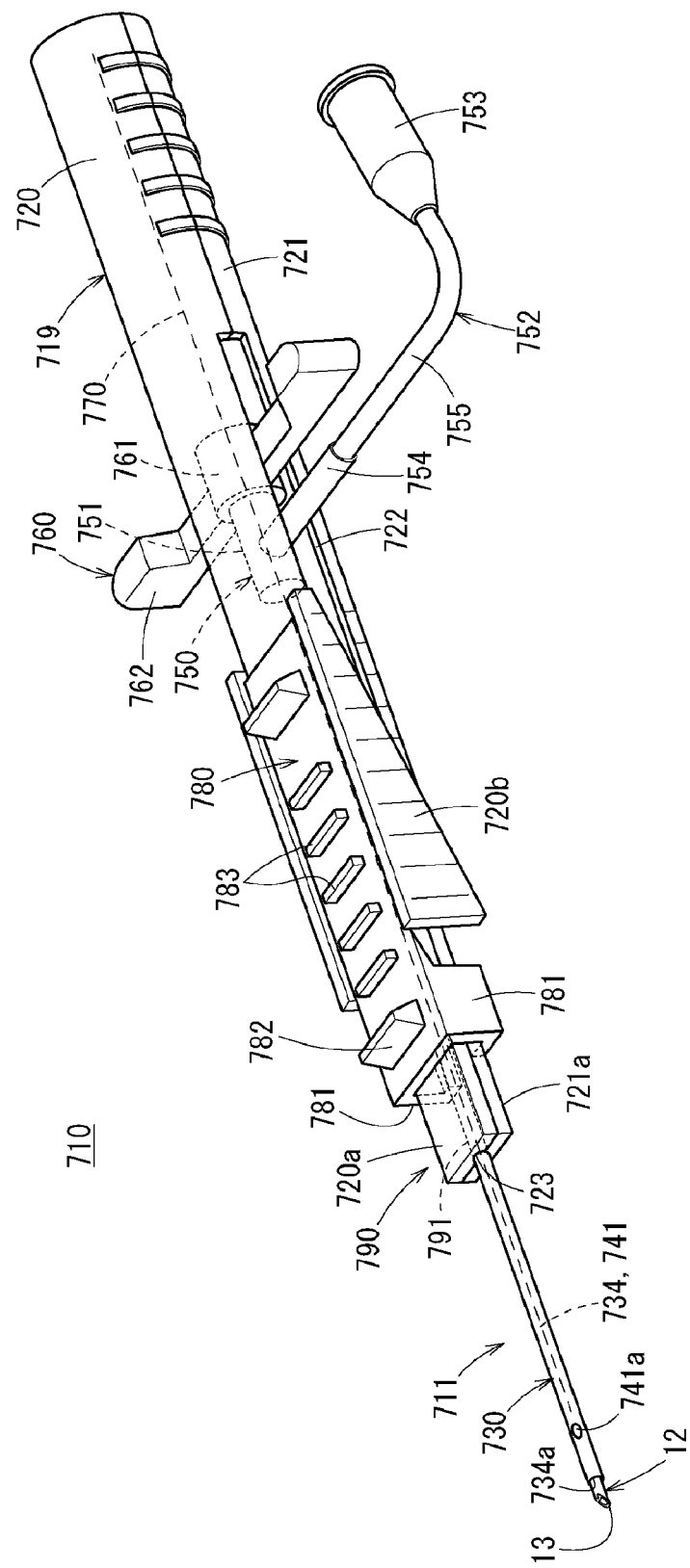
FIG. 13 is a perspective view illustrating an overall configuration of a catheter assembly according to a seventh embodiment.

As illustrated in FIG. 13, a catheter 730 of the catheter assembly 710 according to a seventh embodiment is similar in configuration to the catheter 30 of the first embodiment and a main lumen 734 and a sub lumen 741 are provided in the catheter 730. A deflection suppression mechanism 790 suppressing deflection of the inner needle 12 and the catheter 730 (multi-structure needle 711) is provided on the distal end side of the catheter assembly 710.

Specifically, an inner needle hub 719 has an upper housing 720 and a lower housing 721. In the pre-puncture state, the upper housing 720 and the lower housing 721 overlap each other in the upward-downward direction. Respective distal end portions 720a and 721a of the upper housing 720 and the lower housing 721 are held so as to be embraced by a guide wire operation member 780, which will be described later, and upward-downward expansion is regulated as a result. A slit 722, which extends in the longitudinal direction, is formed between the upper housing 720 and the lower housing 721 in the left and right side portions of the inner needle hub 719. The upper housing 720 has a pair of side grip portions 720b obliquely inclined with respect to the slit 722. The pair of side grip portions 720b are gripped by a user during puncturing with the multi-structure needle 711.

The distal end portion 720a of the upper housing 720 and the distal end portion 721a of the lower housing 721 constitute the deflection suppression mechanism 790. A holding groove 723 having a semicircular cross section is formed in the facing surfaces of the distal end portions 720a and 721a of the upper housing 720 and the lower housing 721. The wall portion that constitutes the holding groove 723 constitutes a hole-shaped sliding contact support portion 791, which rubs against the catheter 730 when the catheter 730 advances with respect to the inner needle 12. In the initial state of the catheter assembly 710, a slight gap is formed between the outer surface of the catheter 730 and the sliding contact support portion 791.

The catheter 730 has a distal end opening 734a communicating with the main lumen 734 at the distal end of the catheter 730 and has a lateral opening 741a of the sub lumen 741 at a predetermined distance (such as 17 mm or more) from the distal end opening 734a. The catheter 730 is fixed and held by a catheter hub 750.

The catheter hub 750 includes a main hub 751 communicating with the main lumen 734 and a sub port 752 provided on the side surface of the main hub 751. In this case, the sub port 752 has a sub hub 753, a hard tube 754, and a soft tube 755. A medical device can be connected to the sub hub 753. The hard tube 754 is connected to the main hub 751 and protrudes to the outside of the inner needle hub 719. The soft tube 755 extends between the hard tube 754 and the sub hub 753 and is softer than the hard tube 754. The sub port 752 is exposed to the outside via the slit 722 of the inner needle hub 719 with the hard tube 754 of the main hub 751 protruding in the lateral direction.

A catheter operation member 760 is attached to the proximal end side of the catheter hub 750 that is beyond the sub port 752. The catheter operation member 760 has a middle base portion 761 detachably connected to the proximal end portion of the catheter hub 750 and a pair of finger hook portions 762 extending to both sides in the leftward-rightward direction from the middle base portion 761. In the pre-puncture state, the middle base portion 761 is accommodated in the inner needle hub 719 and the finger hook portion 762 protrudes outward in the leftward-rightward direction via the slit 722.

In the pre-puncture state of the catheter assembly 710, the deflection suppression mechanism 790 (sliding contact support portion 791) is positioned on the proximal end side that is beyond the lateral opening 741a of the sub lumen 741. The sliding contact support portion 791 is provided closer to the proximal end side than the lateral opening 741a positioned on the most distal end side.

A guide wire 770 extends in the axial direction in the inner needle 12, protrudes from the proximal end opening (not illustrated) of the inner needle 12, and is connected to the proximal end portion of the guide wire operation member 780 via the connecting portion (not illustrated) that is disposed in the inner needle hub 719. The guide wire operation member 780 is provided so as to be displaceable in the forward-rearward direction with respect to inner needle hub 719. The guide wire operation member 780 has a pair of regulating arms 781 embracing the distal end portion of the inner needle hub 719 in the pre-puncture state. The guide wire operation member 780 has a finger hook tab 782 and a plurality of non-slip ribs 783.

When the catheter assembly 710 configured as described above is used, a user performs puncturing on a patient with the multi-structure needle 711 (inner needle 12, catheter 730). At this time, the deflection suppression mechanism 790 suppresses deflection by supporting the multi-structure needle 711. Subsequently, the user operates the guide wire operation member 780 in the distal direction and causes the guide wire 770 to protrude from the distal end of the inner needle 12 for insertion into a blood vessel. Once the pair of regulating arms 781 move to the distal end side beyond the distal end portion of the inner needle hub 719 as the guide wire operation member 780 is moved in the distal direction, the regulation of the upward-downward expansion of the distal end portion of the upper housing 720 and the distal end portion of the lower housing 721 is released.

Subsequently, the user advances the catheter 730 and the catheter hub 750 by operating the catheter operation member 760 in the distal direction. During this movement, the upper housing 720 is opened with respect to the lower housing 721 by the pair of side grip portions 720b coming into contact with the hard tube 754 of the catheter hub 750 and being pressed upward. As a result, the catheter operation member 760 is allowed to move in the distal direction and the catheter 730 can be inserted well into the blood vessel.

The user removes the inner needle 12 from the catheter 730 by pulling the inner needle hub 719 in the proximal direction with respect to the catheter 730 and the catheter hub 750. As a result, the catheter 730 and the catheter hub 750 are indwelled on the patient side.

As described above, the catheter assembly 710 according to the seventh embodiment is capable of obtaining effects similar to those of the embodiments described above. In other words, the deflection suppression mechanism 790 supports the proximal end side of the lateral opening 741a of the sub lumen 741 (sub opening at the most distal end). As a result, damage to the catheter 730 can be reduced and deflection of the inner needle 12 can be suppressed at the same time.

In the catheter assembly 710, the inner needle hub 719 has the slit 722, and thus the sub port 752 can be easily moved along the slit 722 even in the configuration in which the catheter hub 750 is provided with the sub port 752. In other words, a movement of the catheter 730 with respect to the inner needle 12 can be performed with smoothness. In the catheter assembly 710 in particular, the sub port 752 protrudes in the lateral direction of the inner needle hub 719, and thus the sub port 752 becoming a hindrance during puncturing with the multi-structure needle 711 or the like can be suppressed and a user's work can be facilitated. Further, the sub port 752 of the catheter assembly 710 allows the catheter hub 750 to be smoothly moved because the hard tube 754 is placed at the position coming into contact with the inner needle hub 719.

Eighth Embodiment

Figure 14:
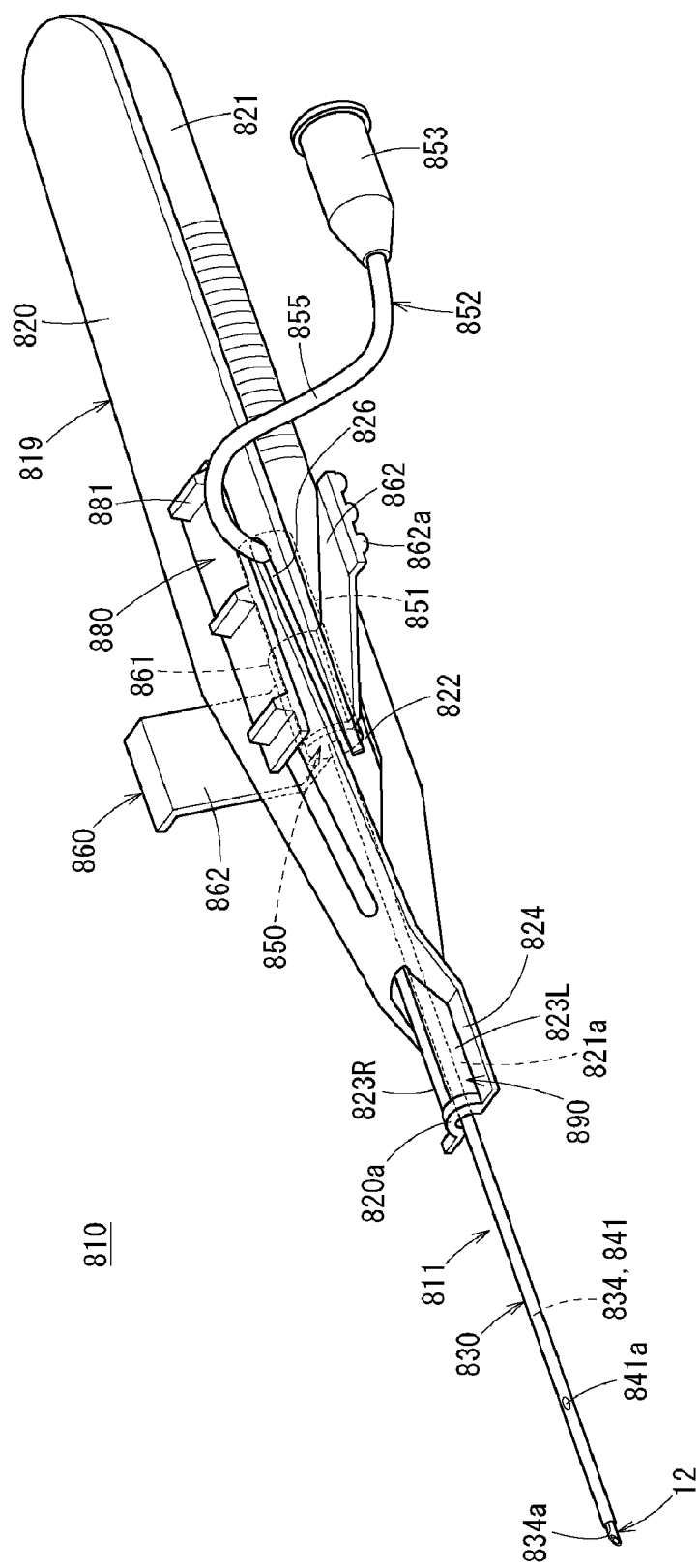
FIG. 14 is a perspective view illustrating an overall configuration of a catheter assembly according to an eighth embodiment.
Figure 15:
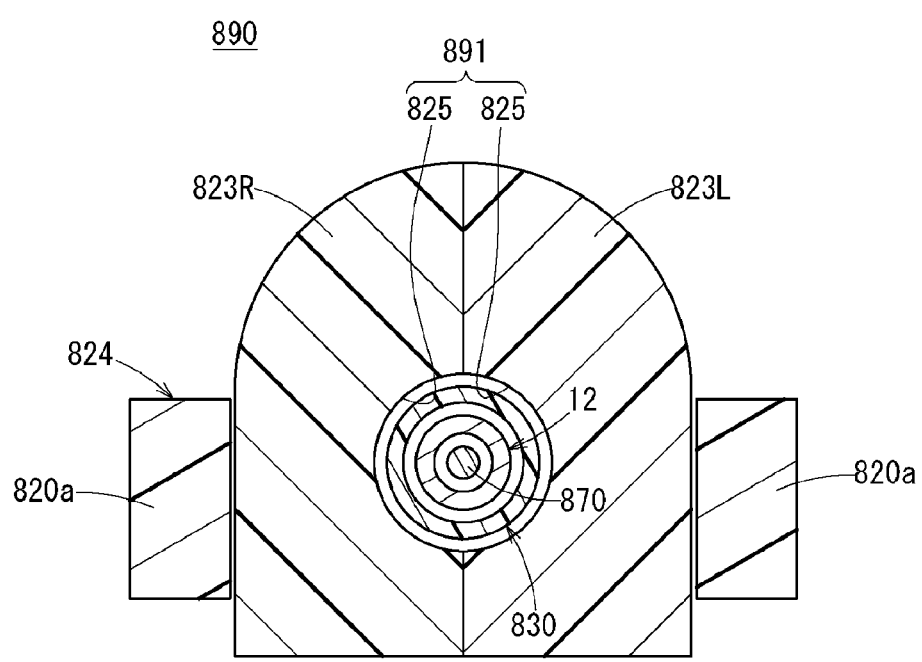
FIG. 15 is a partial cross-sectional view illustrating a deflection suppression mechanism in FIG. 14.

As illustrated in FIGS. 14 and 15, the catheter assembly 810 according to an eighth embodiment is configured by a catheter hub 850 extending to the proximal end side beyond a catheter operation member 860 and a sub port 852 being provided at the extending part of the catheter hub 850. It should be noted that a catheter 830 has a main lumen 834 and a sub lumen 841 as in the first embodiment and constitutes a multi-structure needle 811 by accommodating the inner needle 12 in the pre-puncture state. The catheter 830 has a distal end opening 834a communicating with the main lumen 834 at the distal end of the catheter 830. The catheter 830 has a lateral opening 841a communicating with the sub lumen 841 at a predetermined distance (such as 17 mm or more) from the distal end opening 834a.

The sub port 852 of the catheter hub 850 has a sub hub 853 and a soft tube 855 interconnecting a main hub 851 and the sub hub 853.

As in the seventh embodiment, an inner needle hub 819 of the catheter assembly 810 has an upper housing 820 and a lower housing 821 overlapping each other in the upward-downward direction. In the pre-puncture state, distal end portions 820a and 821a of the upper housing 820 and the lower housing 821 are closed. A slit 822 extending in the longitudinal direction of the inner needle hub 819 is formed between the upper housing 820 and the lower housing 821. The distal end portion 821a of the lower housing 821 has a right side distal end portion 823R and a left side distal end portion 823L and is configured to be capable of expanding in the leftward-rightward direction.

The distal end portion 820a of the upper housing 820 has a regulating portion 824, which regulates leftward-rightward opening of the right side distal end portion 823R and the left side distal end portion 823L of the lower housing 821 in the pre-puncture state. The regulating portion 824 is configured to hold the left and right sides of the right side distal end portion 823R and the left side distal end portion 823L with a pair of plate portions (not illustrated) and interconnect the upper sides of the pair of plate portions (not illustrated) with a bridging portion.

The catheter assembly 810 constitutes a deflection suppression mechanism 890 by means of the right side distal end portion 823R and the left side distal end portion 823L. A holding groove 825 is formed in each of the right side distal end portion 823R and the left side distal end portion 823L. The wall portion that constitutes the two holding grooves 825 constitutes a hole-shaped sliding contact support portion 891, which rubs against the catheter 830 when the catheter 830 advances with respect to the inner needle 12. In the initial state of the catheter assembly 810, a slight gap is formed between the outer surface of the catheter 830 and the inner surface of the sliding contact support portion 891. The sliding contact support portion 891 (deflection suppression mechanism 890) supports the proximal end side that is beyond the lateral opening 841a of the sub lumen 841 (sub opening positioned on the most distal end side).

Further, the upper housing 820 is provided with a guide passage 826 extending in the longitudinal direction. The sub port 852 (soft tube 855) of the catheter hub 850 is exposed from the inside of the upper housing 820 to the outside of the upper housing 820 via the guide passage 826.

The catheter operation member 860 has a middle base portion 861 detachably connected to the proximal end portion of the catheter hub 850 and a pair of finger hook portions 862 extending to both sides in the leftward-rightward direction from the middle base portion 861. The pair of finger hook portions 862 are inclined upward toward the outer side in the leftward-rightward direction. The lower surface of the finger hook portion 862 is provided with a plurality of non-slip projections 862a.

The catheter assembly 810 has a guide wire 870 and a guide wire operation member 880. A plurality of finger hook ribs 881 are provided on the upper surface of the guide wire operation member 880. The guide wire operation member 880 is connected to the proximal end portion of the guide wire 870 via the intermediate connecting portion (not illustrated) that is disposed in the inner needle hub 819. The guide wire operation member 880 is provided so as to be displaceable in the forward-rearward direction with respect to upper housing 820.

When the catheter assembly 810 configured as described above is used, a user performs puncturing on a patient with the multi-structure needle 811 (inner needle 12, catheter 830). At this time, the deflection suppression mechanism 890 suppresses deflection by supporting the multi-structure needle 811. Subsequently, the user operates the guide wire operation member 880 in the distal direction and causes the guide wire 870 to protrude from the distal end of the inner needle 12 for insertion into a blood vessel.

Subsequently, the user advances the catheter 830 and the catheter hub 850 by operating the catheter operation member 860 in the distal direction. During this movement, the upper housing 820 is opened with respect to the lower housing 821 by being pressed upward by the catheter operation member 860. By the upper housing 820 being detached, the right side distal end portion 823R and the left side distal end portion 823L of the lower housing 821 can be further separated from each other in the leftward-rightward direction. As a result, the catheter operation member 860 is allowed to move in the distal direction and the catheter 830 can be inserted well into the blood vessel.

The user removes the inner needle 12 from the catheter 830 by pulling the inner needle hub 819 in the proximal direction with respect to the catheter 830 and the catheter hub 850. As a result, the catheter 830 and the catheter hub 850 are indwelled on the patient side.

As described above, the catheter assembly 810 according to the eighth embodiment is capable of obtaining effects similar to those of the embodiments described above. In other words, the deflection suppression mechanism 890 supports the proximal end side of the lateral opening 841a of the sub lumen 841 (sub opening at the most distal end). As a result, damage to the catheter 830 can be reduced and deflection of the inner needle 12 can be suppressed at the same time.

Further, in the catheter assembly 810, the sub port 852 protrudes in the upward direction of the upper housing 820. As a result, gripping of the inner needle hub 819 can be simplified and operability can be enhanced for users.

Ninth Embodiment

Figure 16:
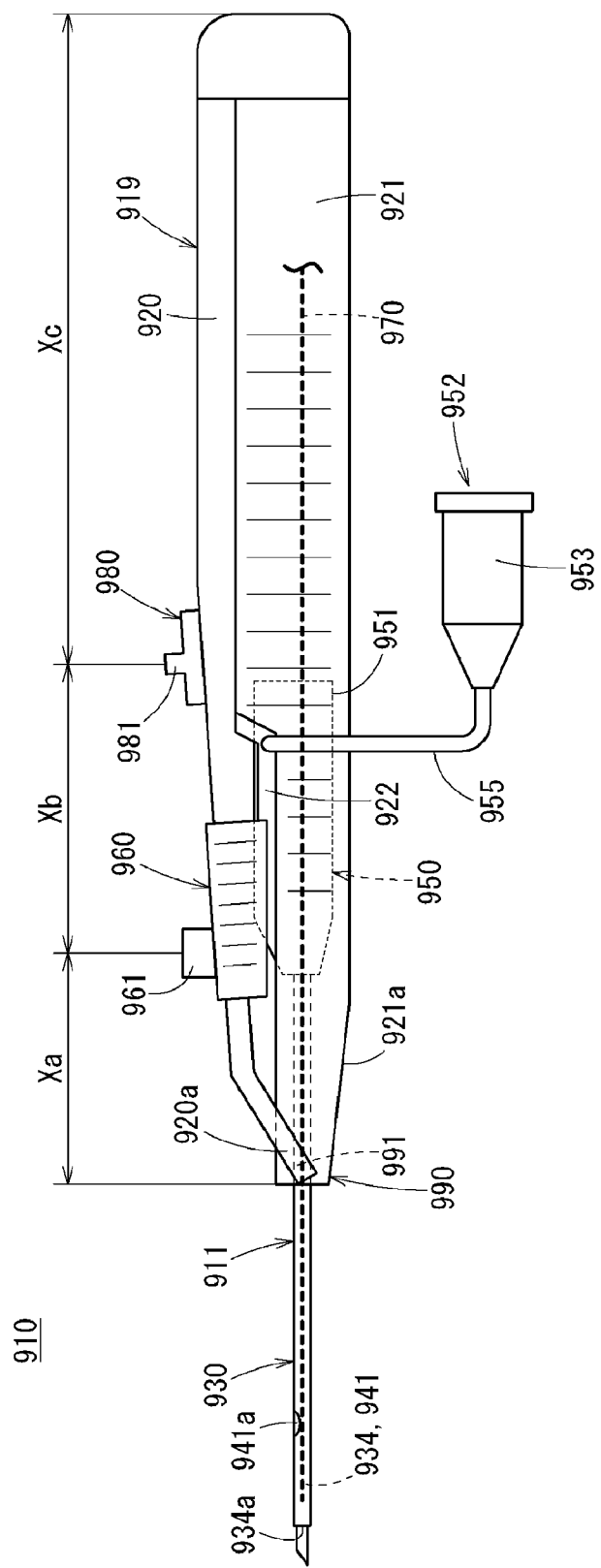
FIG. 16 is a schematic side view illustrating an overall configuration of a catheter assembly according to a ninth embodiment.

As illustrated in FIG. 16, the catheter assembly 910 according to a ninth embodiment is basically similar in configuration to the catheter assembly 810 according to the eighth embodiment and is provided with the inner needle 12, an inner needle hub 919, a catheter 930, a catheter hub 950, a catheter operation member 960, a guide wire 970, a guide wire operation member 980, and a deflection suppression mechanism 990.

The catheter 930 has a main lumen 934 and a sub lumen 941 and constitutes a multi-structure needle 911 by accommodating the inner needle 12 in the pre-puncture state. The catheter 930 has a distal end opening 934a communicating with the main lumen 934 at the distal end of the catheter 930. The catheter 930 has a lateral opening 941a communicating with the sub lumen 941 at a predetermined distance (such as 17 mm or more) from the distal end opening 934a.

The catheter hub 950 is disposed on the proximal end side that is beyond the catheter operation member 960. The catheter hub 950 is configured to be provided with a main hub 951 and a sub port 952 at the extending part of the main hub 951. The sub port 952 has a sub hub 953 and a soft tube 955 interconnecting the main hub 951 and the sub hub 953.

The inner needle hub 919 of the catheter assembly 910 has an upper housing 920 and a lower housing 921 overlapping each other in the upward-downward direction. In the pre-puncture state, distal end portions 920a and 921a of the upper housing 920 and the lower housing 921 are closed. A slit 922 extending in the longitudinal direction of the inner needle hub 919 is formed between the upper housing 920 and the lower housing 921. In the present embodiment, the slit 922 extends to the proximal end side beyond the initial position of the catheter operation member 960 in the pre-puncture state.

The lower housing 921 has a right side distal end portion and a left side distal end portion, which can be separated to the left and right outer sides with separation from the upper housing 920. The right side distal end portion and the left side distal end portion constitute the deflection suppression mechanism 990. As in the eighth embodiment, the deflection suppression mechanism 990 constitutes a sliding contact support portion 991 by means of the holding grooves (not illustrated) of the right side distal end portion and the left side distal end portion. In addition, the deflection suppression mechanism 990 is positioned closer to the proximal end side than the lateral opening 941a positioned on the most distal end side.

The catheter operation member 960 is supported by the upper housing 920 of the inner needle hub 919 so as to be slidable in the forward-rearward direction. A finger hook projection 961 is provided on the upper surface of the catheter operation member 960. The guide wire operation member 980 is displaceable with respect to the upper housing 920 and is connected to the proximal end portion of the guide wire 970 via the intermediate connecting portion (not illustrated) that is disposed in the inner needle hub 919. A plurality of finger hook ribs 981 are provided on the upper surface of the guide wire operation member 980.

In the catheter assembly 910, distances Xa, Xb, and Xc are set to be Xa<Xb<Xc. Xa is the distance from the distal end of the inner needle hub 919 to the projection 961 of the catheter operation member 960. Xb is the distance from the projection 961 to the rib 981. Xc is the distance from the rib 981 to the proximal end of the inner needle hub 919. As a result, with the catheter assembly 910, the position of a finger can be disposed well with respect to each operation member during single-hand operation by a user.

When the catheter assembly 910 configured as described above is used, a user performs puncturing on a patient with the multi-structure needle 911 (inner needle 12, catheter 930). At this time, the deflection suppression mechanism 990 suppresses deflection by supporting the multi-structure needle 911. Subsequently, the user operates the guide wire operation member 980 in the distal direction and causes the guide wire 970 to protrude from the distal end of the inner needle 12 for insertion into a blood vessel.

Subsequently, the user advances the catheter 930 and the catheter hub 950 by operating the catheter operation member 960 in the distal direction. During this movement, the upper housing 920 is opened with respect to the lower housing 921 by being pressed upward by the catheter operation member 960. By the upper housing 920 being detached, the right side distal end portion and the left side distal end portion of the lower housing 921 can be further separated from each other in the leftward-rightward direction. As a result, the catheter operation member 960 is allowed to move in the distal direction and the catheter 930 can be inserted well into the blood vessel.

The user removes the inner needle 12 from the catheter 930 by pulling the inner needle hub 919 in the proximal direction with respect to the catheter 930 and the catheter hub 950. As a result, the catheter 930 and the catheter hub 950 are indwelled on the patient side.

As described above, the catheter assembly 910 according to the ninth embodiment is capable of obtaining effects similar to those of the embodiments described above. In other words, the deflection suppression mechanism 990 supports the proximal end side of the lateral opening 941a of the sub lumen 941 (sub opening at the most distal end). As a result, damage to the catheter 930 can be reduced and deflection of the inner needle 12 can be suppressed at the same time.

Tenth Embodiment

Figure 17:
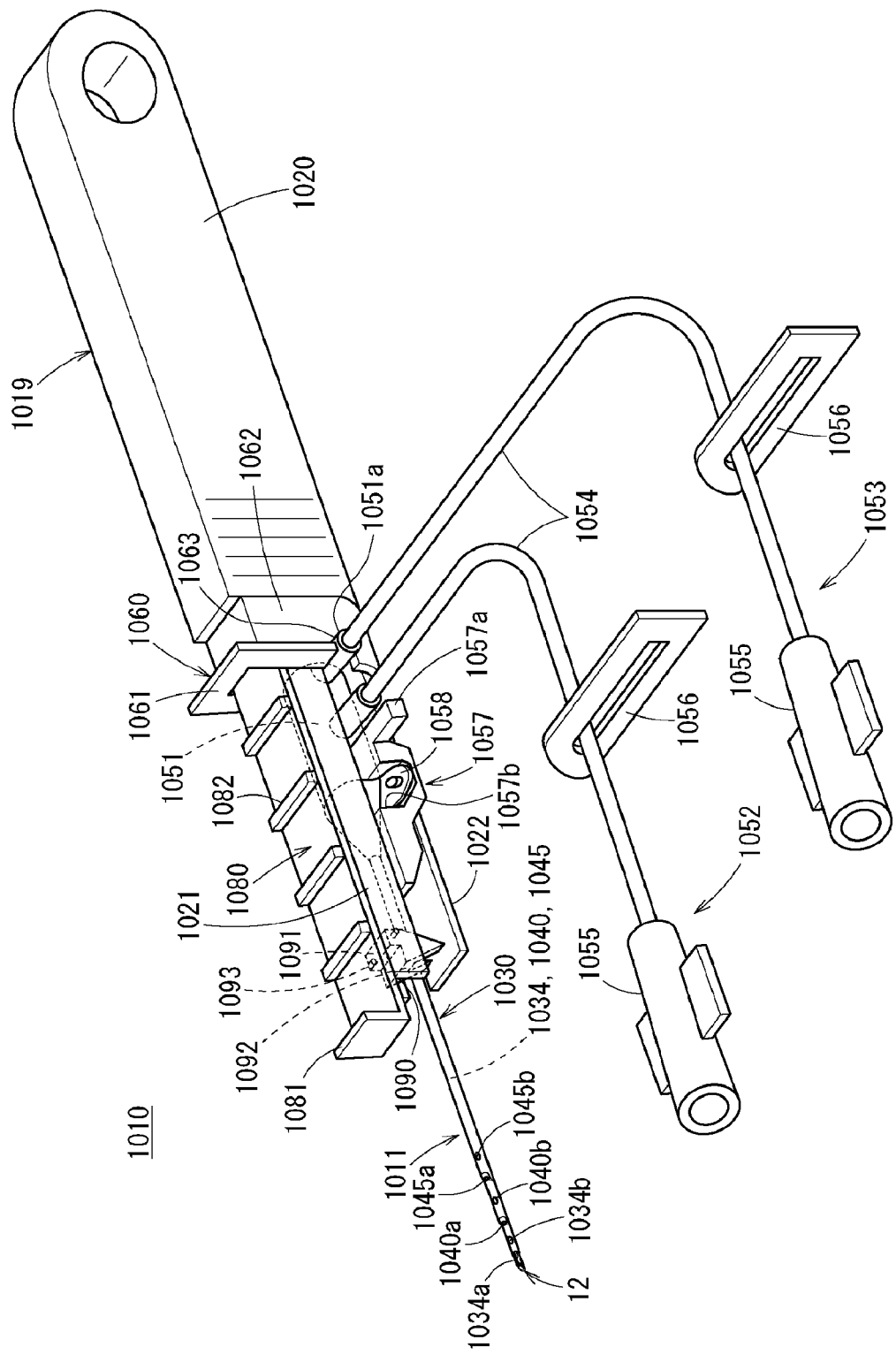
FIG. 17 is a perspective view illustrating an overall configuration of a catheter assembly according to a tenth embodiment.

As illustrated in FIG. 17, the catheter assembly 1010 according to a tenth embodiment is provided with the inner needle 12, a catheter 1030, a catheter hub 1050 connected to the catheter 1030, a catheter operation member 1060 moving the catheter hub 1050 in the distal direction, an inner needle hub 1019 connected to the inner needle 12, a guide wire (not illustrated) inserted through the inner needle 12, a guide wire operation member 1080 connected to the guide wire, and a deflection suppression mechanism 1090 suppressing deflection of the inner needle 12 during puncturing. The inner needle 12 and the catheter 1030 form a multi-structure needle 1011 in the pre-puncture state.

The catheter 1030 is similar in configuration to the fifth embodiment. In other words, the catheter 1030 has a main lumen 1034, a first sub lumen 1040, and a second sub lumen 1045. The main lumen 1034 communicates with a first distal end opening 1034a and a first lateral opening 1034b on the distal end side of the catheter 1030 and communicates with the proximal end opening (not illustrated) that is at the proximal end of the catheter 1030. The first sub lumen 1040 communicates with a second distal end opening 1040a and a second lateral opening 1040b on the distal end side of the catheter 1030 and communicates with the proximal end opening (not illustrated) that is at the proximal end of the catheter 1030. The second sub lumen 1045 communicates with a third distal end opening 1045a and a third lateral opening 1045b on the distal end side of the catheter 1030 and communicates with the proximal end opening (not illustrated) that is at the proximal end of the catheter 1030.

The catheter hub 1050 is fixed to the proximal end portion of the catheter 1030. The catheter hub 1050 is accommodated in the inner needle hub 1019 in the pre-puncture state of the catheter assembly 1010. The catheter hub 1050 has a main hub 1051 connected to the catheter 1030 and a first side port 1052 and a second side port 1053 protruding in the lateral direction (horizontal direction perpendicular to the axis of the main hub 1051) from the main hub 1051. The first and second side ports 1052 and 1053 have a soft tube 1054 connected to the main hub 1051 via a hard tube 1051a and a sub hub 1055 connected to the other end of the soft tube 1054. A clamp 1056, which is capable of opening and closing the communication path in the soft tube 1054, is attached to the soft tube 1054.

The catheter assembly 1010 has a slide member 1057, which slides integrally with the catheter hub 1050 along a housing 1020 (lower side extending portion 1022). The slide member 1057 has a pair of holding projecting portions 1057a, which are gripped by a user during detachment of the catheter hub 1050 from the housing 1020.

The slide member 1057 has an accommodating groove 1057b accommodating the distal end side of the catheter hub 1050. Especially, the catheter hub 1050 according to the present embodiment has a pair of wings 1058 extending outward in the width direction from the outer peripheral surface on the distal end side and the accommodating groove 1057b is formed in a shape that allows the pair of wings 1058 to be stored. The wing 1058 is provided with a small hole (not illustrated). The convex portion (not illustrated) that is provided in the accommodating groove 1057b is inserted into the small hole. The accommodating groove 1057b is open upward, and the catheter hub 1050 can be detached upward.

The catheter operation member 1060 is an annular member supported so as to be slidable in the forward-rearward direction in the distal end portion of the housing 1020 of the inner needle hub 1019, which will be described later. The catheter operation member 1060 is provided with a finger hook portion 1061 protruding in a flange shape. A side wall 1062 of the catheter operation member 1060 is provided with a recess portion 1063 open in the distal direction. The second side port 1053 of the catheter hub 1050 protrudes in the lateral direction via the recess portion 1063.

The inner needle hub 1019 has the housing 1020 functioning as a grip portion for a user and an upper side extending portion 1021 and the lower side extending portion 1022 extending in parallel to each other in the distal direction from the distal end portion of the housing 1020. In the pre-puncture state of the catheter assembly 1010, the catheter 1030 and the catheter hub 1050 are disposed between the upper side extending portion 1021 and the lower side extending portion 1022.

The deflection suppression mechanism 1090 is provided in the distal end portion of the inner needle hub 1019. Specifically, the deflection suppression mechanism 1090 is provided with a support member 1091, which is supported by the upper side extending portion 1021 so as to be rotatable about an axis in the leftward-rightward direction. The support member 1091 has a sliding contact support portion 1092, which rubs against the catheter 1030 when the catheter 1030 advances with respect to the inner needle 12. An upper portion 1091u of the support member 1091 is provided with a shaft portion 1093. The shaft portion 1093 is pivotally supported by the upper side extending portion 1021. The distal end portion of the guide wire operation member 1080 is positioned closer to the distal end side than the upper portion 1091u of the support member 1091. Accordingly, upward rotation of the support member 1091 is regulated by the guide wire operation member 1080.

Figure 18:
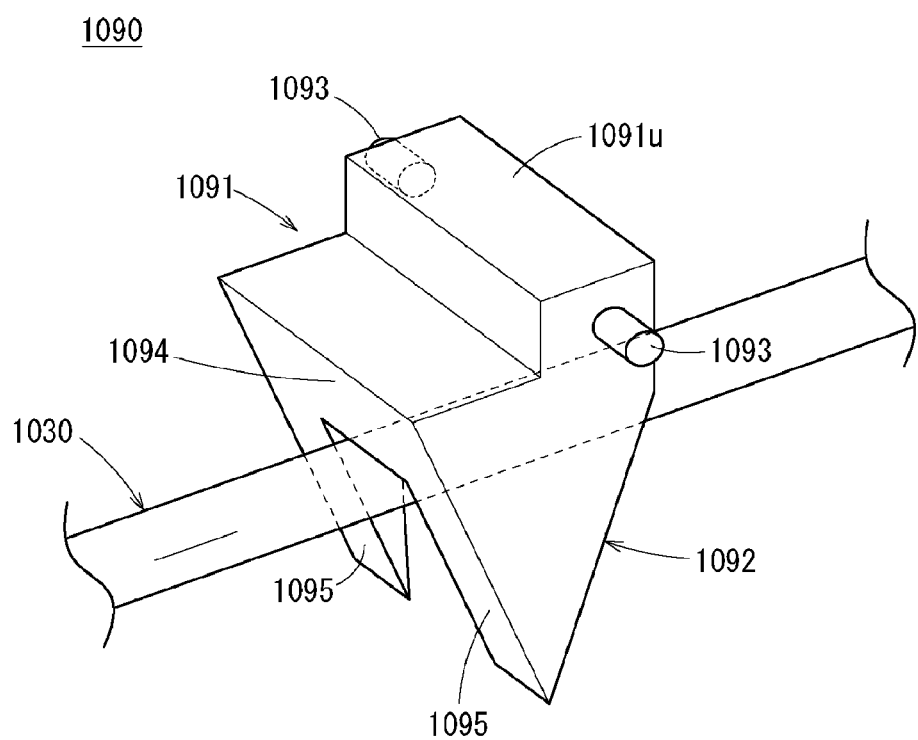
FIG. 18 is an enlarged perspective view illustrating a deflection suppression mechanism in FIG. 17.

As illustrated in FIG. 18, the sliding contact support portion 1092 has an upper support portion 1094 capable of supporting the catheter 1030 from above and left and right lateral support portions 1095 capable of supporting the catheter 1030 from the lateral direction. The lateral support portions 1095 protrude downward from the left and right end portions of the upper support portion 1094. Accordingly, the sliding contact support portion 1092 is formed in an inverted U-shape as viewed from the longitudinal direction of the catheter assembly 1010. In the pre-puncture state, a slight gap is formed between the outer surface of the catheter 1030 and the sliding contact support portion 1092.

As illustrated in FIG. 17, in the initial state of the catheter assembly 1010, the sliding contact support portion 1092 supports the proximal end side that is beyond the third lateral opening 1045b positioned on the most distal end side.

The guide wire operation member 1080 is an operation portion for performing guide wire insertion into a patient's blood vessel prior to insertion of the catheter 1030 into the blood vessel. A finger hook projection 1081 and a plurality of non-slip ribs 1082 are provided at the distal end of the guide wire operation member 1080. The guide wire operation member 1080 is supported so as to be slidable in the forward-rearward direction on the upper surface of the upper side extending portion 1021. One end portion of the guide wire is disposed in the vicinity of the distal end of the inner needle 12 and the other end portion of the guide wire is connected to the guide wire operation member 1080. The intermediate portion of the guide wire is folded back in the housing 1020.

A patient's skin is punctured with the catheter assembly 1010 when the catheter assembly 1010 is used. A user performs the skin puncturing toward a puncturing target blood vessel by pressing the distal end portion of the catheter assembly 1010 against the patient with the housing 1020 in the pre-puncture state illustrated in FIG. 17 gripped. As a result, the skin is punctured with the respective distal end portions of the inner needle 12 and the catheter 1030.

Once the user subsequently moves the guide wire operation member 1080 in the proximal direction, the guide wire intermediately folded back in the housing 1020 moves in the distal direction in the inner needle 12. As a result, the guide wire protrudes from the distal end of the inner needle 12 and is inserted into the blood vessel. As the guide wire operation member 1080 is moved in the proximal direction, the distal end portion of the guide wire operation member 1080 moves in the proximal direction beyond the upper portion of the support member 1091. As a result, the regulation of upward rotation of the support member 1091 by the guide wire operation member 1080 is released.

After the distal end of the guide wire is inserted into the target position in the blood vessel, the user advances the catheter 1030, the catheter hub 1050, and the slide member 1057 by operating the catheter operation member 1060 in the distal direction with the position of the inner needle hub 1019 fixed. As a result, the catheter 1030 is inserted into the target position in the blood vessel. At this time, the support member 1091 rotates upward by being pressed by the slide member 1057 moving in the distal direction. As a result, the catheter 1030 is allowed to be detached in the distal direction from the inner needle hub 1019.

Subsequently, the user pulls the housing 1020 in the proximal direction with the positions of the catheter 1030, the catheter hub 1050, and the slide member 1057 held by pressing the pair of holding projecting portions 1057a of the slide member 1057. As a result, the catheter 1030, the catheter hub 1050, and the slide member 1057 completely come out of the inner needle hub 1019 and the inner needle 12 is removed in the proximal direction from the catheter 1030. Subsequently, the catheter hub 1050 is removed from the slide member 1057. Then, a tape or the like (not illustrated) is attached to the pair of wings 1058 of the catheter hub 1050. As a result, the catheter 1030 and the catheter hub 1050 are indwelled in the patient's blood vessel.

As described above, the catheter assembly 1010 according to the tenth embodiment is capable of obtaining effects similar to those of the embodiments described above. In other words, the deflection suppression mechanism 1090 supports the proximal end side of the third lateral opening 1045b of the second sub lumen 1045 (sub opening at the most proximal end). As a result, damage to the catheter 1030 can be reduced and deflection of the inner needle 12 can be suppressed at the same time.

The sliding contact support portion 1092, in particular, has the upper support portion 1094 capable of supporting the catheter 1030 from above and the lateral support portion 1095 capable of supporting the catheter 1030 from the lateral direction (FIG. 18) and the third lateral opening 1045b is provided in any place in the upper and lateral portions of the catheter 1030. With this configuration, it is possible to effectively suppress damage to the third lateral opening 1045*b* and an increase in sliding resistance during advancement of the catheter 1030.

It should be noted that each of the configurations described in the first to tenth embodiments and the first to eighth configuration examples of the present invention can be partially taken out and applied to another embodiment or another configuration example without departing from the technical idea of the present invention.

What is claimed is:

1. A catheter assembly comprising:
a catheter comprising a main lumen and one or more sub lumens provided separately from the main lumen; and
an inner needle extending through the main lumen; and
a deflection suppression mechanism configured to suppress deflection of the inner needle by supporting the inner needle via the catheter;
wherein the one or more sub lumens respectively communicate with one or more sub openings formed in the catheter;
wherein the catheter is configured to advance with respect to the inner needle;
wherein the deflection suppression mechanism comprises a contact support portion that contacts the catheter when the catheter advances with respect to the inner needle; and
wherein the contact support portion is configured to contact the catheter at (i) a location proximal of a distal-most one of the one or more sub openings, and/or (ii) a location proximal of a step portion generated in the catheter as the one or more sub lumens are formed.

2. The catheter assembly according to claim 1, wherein:
the deflection suppression mechanism is configured to contact the catheter at a location proximal of a proximal-most one of the one or more sub openings.

3. The catheter assembly according to claim 1, wherein:
the main lumen and the one or more sub lumens extend parallel to each other in the catheter.

4. The catheter assembly according to claim 1, wherein:
the step portion is a tapered portion gradually decreasing in outer diameter toward a distal direction;
the one or more sub openings are provided in the tapered portion; and
the deflection suppression mechanism is configured to contact the catheter at a location proximal of the tapered portion.

5. The catheter assembly according to claim 1, wherein:
the one or more sub openings include a lateral opening provided in an outer peripheral surface of the catheter; and
the deflection suppression mechanism is configured to contact the catheter at a location of the lateral opening.

6. The catheter assembly according to claim 1, wherein:
the main lumen communicates with a main opening formed in the catheter; and
the main opening and the one or more sub openings are spaced apart from each other at a distance of 17 mm or more.

7. The catheter assembly according to claim 1, wherein:
the deflection suppression mechanism is configured to contact the catheter at a distal end side of the deflection suppression mechanism, and at a distance of 5 mm or less from a closest of the one or more sub openings.

8. The catheter assembly according to claim 1, wherein:
the main lumen and the one or more sub lumens are partitioned from each other by a partition wall that is deformable in response to pressure.

9. The catheter assembly according to claim 1, wherein:
the deflection suppression mechanism surrounds an entire circumference of the catheter.

10. The catheter assembly according to claim 1, further comprising:
a catheter hub fixing and holding the catheter; and
an inner needle hub fixing and holding the inner needle;
wherein the one or more sub lumens communicate with communication paths of one or more ports provided in the catheter hub; and
wherein each of the one or more ports is configured as a connector to which a medical device is connectable.

11. The catheter assembly according to claim 10, wherein:
the inner needle hub is configured as a housing movably accommodating the catheter hub; and
the housing comprises a slit exposing the one or more ports from an inside of the housing to an outside of the housing.

12. The catheter assembly according to claim 11, wherein:
the housing is separable upward and downward;
the slit constitutes apart of a boundary at which the housing is separable upward and downward; and
the one or more ports protrude in a lateral direction of the housing.

13. The catheter assembly according to claim 10, wherein:
The one or more ports protrude in an upward direction of the inner needle hub.

14. The catheter assembly according to claim 10, wherein:
each of the one or more ports comprises:
a connecting portion to which the medical device is connectable, and
a soft tube extending between the catheter hub and the connecting portion and being softer than the connecting portion.

15. The catheter assembly according to claim 10, wherein:
each of the one or more ports comprises:
a connecting portion to which the medical device is connectable,
a hard tube connected to the catheter hub and protruding to an outside of the inner needle hub, and
a soft tube extending between the hard tube and the connecting portion and being softer than the connecting portion.

* * * * *